(12) United States Patent
Hashimoto et al.

(10) Patent No.: US 9,101,618 B2
(45) Date of Patent: Aug. 11, 2015

(54) METHOD FOR TREATING AND/OR PREVENTING NEURODEGENERATIVE DISEASE BY ADIPONECTIN RECEPTOR AGONIST

(75) Inventors: Makoto Hashimoto, Tokyo (JP); Kazunari Sekiyama, Tokyo (JP); Yoshiki Takamatsu, Tokyo (JP); Masayo Fujita, Tokyo (JP); Akio Sekigawa, Tokyo (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 0 days.

(21) Appl. No.: 13/590,065

(22) Filed: Aug. 20, 2012

(65) Prior Publication Data
US 2013/0157950 A1    Jun. 20, 2013

(30) Foreign Application Priority Data
Dec. 15, 2011  (JP) ................................. 2011-274797

(51) Int. Cl.
| | | |
|---|---|---|
| A61P 25/28 | (2006.01) | |
| A61P 25/14 | (2006.01) | |
| A61P 25/00 | (2006.01) | |
| A61K 31/4439 | (2006.01) | |
| A61K 38/22 | (2006.01) | |

(52) U.S. Cl.
CPC .............. *A61K 31/4439* (2013.01); *A61K 38/22* (2013.01)

(58) Field of Classification Search
None
See application file for complete search history.

(56) References Cited

U.S. PATENT DOCUMENTS

| | | | |
|---|---|---|---|
| 2004/0023854 A1* | 2/2004 | Cooper et al. | 514/8 |
| 2006/0128610 A1* | 6/2006 | Cooper | 514/8 |
| 2007/0203061 A1 | 8/2007 | Kadowaki et al. | |

FOREIGN PATENT DOCUMENTS

| | | |
|---|---|---|
| JP | 2008-105945 | 5/2008 |
| JP | 2008-195630 | 8/2008 |
| JP | 2011-148748 | 8/2011 |

(Continued)

OTHER PUBLICATIONS

Swanson et al., The PPAR-gamma agonist pioglitazone modulates inflammation and induces neuroprotection in parkinsonian monkeys. Journal of Neuroinflammation 2011, 8:91, 1-14.*

(Continued)

*Primary Examiner* — Gregory S Emch
*Assistant Examiner* — Aurora M Fontainhas
(74) *Attorney, Agent, or Firm* — Birch, Stewart, Kolasch & Birch, LLP

(57) ABSTRACT

The present invention was accomplished for the purpose of developing a method for effectively treating and/or preventing synucleinopathies, and is based on a discovery that an adiponectin receptor agonist suppresses α (alpha)-synuclein aggregation, tau phosphorylation and a decrease in proteasomal activity.

The method of the present invention for treating and/or preventing neurodegenerative diseases includes a step of administering an effective dose of at least one effective element selected from a group consisting of: adiponectin as an adiponectin receptor agonist; a compound inducing expression of adiponectin; globular adiponectin; and a compound inducing expression of globular adiponectin. The present invention further provides a screening method of the adiponectin receptor agonist for treating and/or preventing neurodegenerative diseases.

20 Claims, 17 Drawing Sheets

(56) References Cited

FOREIGN PATENT DOCUMENTS

| JP | 2011-236236 | 11/2011 |
|----|-------------|---------|
| WO | 2005094866  | 10/2005 |

OTHER PUBLICATIONS

Bodies et al., Pioglitazone increases secretion of high-molecular-weight adiponectin from adipocytes. Am J Physiol Endocrinol Metab 291:E1100-E1105, 2006.*

Thundyil et al., Adiponectin receptor signalling in the brain. British Journal of Pharmacology (2012) 165 313-327.*

Spillantini et al., alpha-Synuclein in filamentous inclusions of Lewy bodies from Parkinson's disease and dementia with Lewy bodies. Proc. Natl. Acad. Sci. vol. 95, pp. 6469-6473, May 1998.*

Calne D.B. et al., Criteria for Diagnosing Parkinson's Disease, Ann Neurol 1992; 32:S125-S127.

Kazuhisa Maeda et al., cDNA Cloning and Expression of a Novel Adipose Specific Collagen-Like Factor, apM1 (Adipose Most Abundant Gene Transcript 1), Biochemical and Biophysical Research Communications 221, 286-289 (1996).

Makoto Hashimoto et al., Human Recombinant NACP/Alpha-Synuclein Is Aggregated and Fibrillated In Vitro: Relevance for Lewy Body Disease, Brain Research 799 (1998), 301-306.

Makoto Hashimoto et al., Symposium: Tau and Synuclein in Neuropathology, Alpha-Synuclein in Lewy Body Disease and Alzheimer's Disease, Brain Pathology 9: 707-720 (1999).

Edward Rockenstein et al., Early Formation of Mature Amyloid-Beta Protein Deposits in a Mutant App Transgenic Model Depends on Levels of A-beta 1-42, Journal of Neuroscience Research 66:573-582 (2001).

Takato Takenouchi et al., Reduced Neuritic Outgrowth and Cell Adhesion in Neuronal Cells Transfected With Human Alpha-Synuclein, Molecular and Cellular Neuroscience 17, 141-150 (2001).

I.G. McKeith et al., Diagnosis and Management of Dementia With Lewy Bodies, Third Report of the DLB consortium, Neurology 65 (Dec. 2005), pp. 1863-1872.

Masayo Fujita, A Beta-Synuclein Mutation Linked to Dementia Produces Neurodegeneration When Expressed in Mouse Brain, Nature Communications 1:110 (DOI: 10.1038/ncomms1101), Published Nov. 2, 2010.

Yatomi, K, et al, "Pathophysiological dual action of adiponectin after transient focal ischemia in mouse brain", Brain Research 1297 (2009), pp. 169-176.

Tanaka, K et al, "Regional alterations in glucose consumption and metabolite levels during postischemic recovery in cat brain", Journal of Cerebral Blood Flow and Metabolism 5 (1985) pp. 502-511.

Stefanovich, V. "Energy metabolism in the brain", Z Gerontol. Jul.-Aug. 1985;18 (4):2105 (English abstract only).

Actos (pioglitazone hydrochloride) Package Insert and Medication Guide; Takeda Pharmaceuticals America, Inc., Jul. 2011.

Kadowaki, T, et al. "The physiological and pathophysiological role of adiponectin and adiponectin receptors in the peripheral tissues and CNS"; FEBS Letters 582 (2008), pp. 74-80.

Jellinger, Kurt A. "α-Synuclein pathology in Parkinson's and Alzheimer's disease brain: incidence and topographic distribution—a pilot study," Acta Neuropathol (2003) 106:191-202.

Leverenz, James et al. "Lewy Body Pathology in Familial Alzheimer Disease," Arch Neurol. (Mar. 2006) 63:370-376.

Serrano-Pozo, Alberto et al. "Neuropathological Alterations in Alzheimer Disease," Cold Spring Harbor Perspectives in Medicine (2011) 1:a006189.

Wilson, Christina et al. "Degradative organelles containing mislocalized α- and β-synuclein proliferate in presenilin-1 null neurons," J. Cell Biol. (2004) 165:335-346.

Winslow, Ashley et al. "Convergence of pathology in dementia with Lewy bodies and Alzheimer's disease: a role for the novel interaction of alpha-synuclein and presenilin 1 in disease," Brain (2014) 137:1958-1970.

Yoshimoto, Makoto et al. "NACP, the precursor protein of the non-amyloid β/A4 protein (Aβ) component of Alzheimer disease amyloid, binds Aβ and stimulates Aβ aggregation," Proc. Natl. Acad. Sci. USA (Sep. 1995) 92: 9141-9145.

\* cited by examiner

SEQUENCE LISTING

```
<160> NUMBER OF SEQ ID NOS: 24

<210> SEQ ID NO 1
<211> LENGTH: 24
<212> TYPE: DNA
<213> ORGANISM: Artificial
<220> FEATURE:
<223> OTHER INFORMATION: mouse adiponectin forward primer

<400> SEQUENCE: 1
ctacaactga agagctagct cctg                                          24

<210> SEQ ID NO 2
<211> LENGTH: 24
<212> TYPE: DNA
<213> ORGANISM: Artificial
<220> FEATURE:
<223> OTHER INFORMATION: mouse adiponectin reverse primer

<400> SEQUENCE: 2
cacactgaac gctgagcgat acac                                          24

<210> SEQ ID NO 3
<211> LENGTH: 26
<212> TYPE: DNA
<213> ORGANISM: Artificial
<220> FEATURE:
<223> OTHER INFORMATION: rat adiponectin forward primer

<400> SEQUENCE: 3
ggacaacaat ggactctatg cagata                                        26

<210> SEQ ID NO 4
<211> LENGTH: 24
<212> TYPE: DNA
<213> ORGANISM: Artificial
<220> FEATURE:
<223> OTHER INFORMATION: rat adiponectin reverse primer

<400> SEQUENCE: 4
ctacgggctg ctctgaatta ggtg                                          24

<210> SEQ ID NO 5
<211> LENGTH: 24
<212> TYPE: DNA
<213> ORGANISM: Artificial
<220> FEATURE:
<223> OTHER INFORMATION: mouse adiponectin receptor 1 forward primer
```

-continued

```
<400> SEQUENCE: 5
caacatctgg acacatctgc ttgg                                          24

<210> SEQ ID NO 6
<211> LENGTH: 25
<212> TYPE: DNA
<213> ORGANISM: Artificial
<220> FEATURE:
<223> OTHER INFORMATION: mouse adiponectin receptor 1 reverse primer

<400> SEQUENCE: 6
gtagagcaat ccctgaatag tccag                                         25

<210> SEQ ID NO 7
<211> LENGTH: 21
<212> TYPE: DNA
<213> ORGANISM: Artificial
<220> FEATURE:
<223> OTHER INFORMATION: rat adiponectin receptor 1 forward primer

<400> SEQUENCE: 7
atcttccgca tccacacaga a                                             21

<210> SEQ ID NO 8
<211> LENGTH: 24
<212> TYPE: DNA
<213> ORGANISM: Artificial
<220> FEATURE:
<223> OTHER INFORMATION: rat adiponectin receptor 1 reverse primer

<400> SEQUENCE: 8
atatttggtc tgagcatggt caag                                          24

<210> SEQ ID NO 9
<211> LENGTH: 25
<212> TYPE: DNA
<213> ORGANISM: Artificial
<220> FEATURE:
<223> OTHER INFORMATION: mouse adiponectin receptor 2 forward primer

<400> SEQUENCE: 9
ttggacacat ctcctaggtt gtgta                                         25

<210> SEQ ID NO 10
<211> LENGTH: 26
<212> TYPE: DNA
<213> ORGANISM: Artificial
<220> FEATURE:
<223> OTHER INFORMATION: mouse adiponectin receptor 2 reverse primer

<400> SEQUENCE: 10
cacagatgac aatcaggtag atgaag                                        26

<210> SEQ ID NO 11
<211> LENGTH: 23
<212> TYPE: DNA
<213> ORGANISM: Artificial
<220> FEATURE:
<223> OTHER INFORMATION: rat adiponectin receptor 2 forward primer

<400> SEQUENCE: 11
agataggctg gctaatgctc atg                                           23
```

```
<210> SEQ ID NO 12
<211> LENGTH: 22
<212> TYPE: DNA
<213> ORGANISM: Artificial
<220> FEATURE:
<223> OTHER INFORMATION: rat adiponectin receptor 2 reverse primer

<400> SEQUENCE: 12
gatgtcacat ttgccaggaa ag                                              22

<210> SEQ ID NO 13
<211> LENGTH: 19
<212> TYPE: DNA
<213> ORGANISM: Artificial
<220> FEATURE:
<223> OTHER INFORMATION: mouse and rat cyclophilin A forward primer

<400> SEQUENCE: 13
tccatggcaa atgctggac                                                  19

<210> SEQ ID NO 14
<211> LENGTH: 20
<212> TYPE: DNA
<213> ORGANISM: Artificial
<220> FEATURE:
<223> OTHER INFORMATION: mouse and rat cyclophilin A reverse primer

<400> SEQUENCE: 14
gtcttgccat tcctggaccc                                                 20

<210> SEQ ID NO 15
<211> LENGTH: 21
<212> TYPE: DNA
<213> ORGANISM: Artificial
<220> FEATURE:
<223> OTHER INFORMATION: adiponectin sense siRNA

<400> SEQUENCE: 15
caaugacucu cacauuuacat t                                              21

<210> SEQ ID NO 16
<211> LENGTH: 21
<212> TYPE: DNA
<213> ORGANISM: Artificial
<220> FEATURE:
<223> OTHER INFORMATION: adiponectin antisense siRNA

<400> SEQUENCE: 16
uguaaaugua gagucauugt t                                               21

<210> SEQ ID NO 17
<211> LENGTH: 21
<212> TYPE: DNA
<213> ORGANISM: Artificial
<220> FEATURE:
<223> OTHER INFORMATION: randam sense siRNA

<400> SEQUENCE: 17
ucuuaaucgc guauaaggct t                                               21

<210> SEQ ID NO 18
<211> LENGTH: 21
<212> TYPE: DNA
<213> ORGANISM: Artificial
<220> FEATURE:
<223> OTHER INFORMATION: randam antisense siRNA
```

```
<400> SEQUENCE: 18
gccuuauacg cgauuaagat t                                          21

<210> SEQ ID NO 19
<211> LENGTH: 21
<212> TYPE: DNA
<213> ORGANISM: Artificial
<220> FEATURE:
<223> OTHER INFORMATION: adiponectin N-terminal primer for constructing
      expression vector

<400> SEQUENCE: 19
gggatgctac tgttgcaagc t                                          21

<210> SEQ ID NO 20
<211> LENGTH: 27
<212> TYPE: DNA
<213> ORGANISM: Artificial
<220> FEATURE:
<223> OTHER INFORMATION: adiponectin C-terminal primer for constructing
      expression vector

<400> SEQUENCE: 20
gagtagttgc agtcagttgg tatcatg                                    27

<210> SEQ ID NO 21
<211> LENGTH: 735
<212> TYPE: DNA
<213> ORGANISM: Homo sapiens
<220> FEATURE:
<221> NAME/KEY: misc_feature
<223> OTHER INFORMATION: adiponectin nucleotide sequence

<400> SEQUENCE: 21
atgctgttgc tgggagctgt tctactgcta ttagctctgc ccggtcatga ccaggaaacc    60
acgactcaag ggcccggagt cctgcttccc ctgcccaagg gggcctgcac aggttggatg   120
gcgggcatcc cagggcatcc gggccataat ggggccccag gccgtgatgg cagagatggc   180
acccctggtg agaagggtga gaaggagat ccaggtctta ttggtcctaa gggagacatc    240
ggtgaaaccg gagtacccgg ggctgaaggt ccccgaggct ttccgggaat ccaaggcagg   300
aaaggagaac ctggagaagg tgcctatgta taccgctcag cattcagtgt gggattggag   360
acttacgtta ctatccccaa catgcccatt cgctttacca agatcttcta caatcagcaa   420
aaccactatg atgctccac tggtaaattc cactgcaaca ttcctgggct gtactacttt    480
gcctaccaca tcacagtcta tatgaaggat gtgaaggtca gcctcttcaa gaaggacaag   540
gctatgctct tcacctatga tcagtaccag gaaaataatg tggaccaggc ctccggctct   600
gtgctcctgc atctggaggt gggcgaccaa gtctggctcc aggtgtatgg ggaaggagag   660
cgtaatggac tctatgctga taatgacaat gactccacct tcacaggctt tcttctctac   720
catgacacca actga                                                    735

<210> SEQ ID NO 22
<211> LENGTH: 244
<212> TYPE: PRT
<213> ORGANISM: Homo sapiens
<220> FEATURE:
<221> NAME/KEY: MISC_FEATURE
<223> OTHER INFORMATION: adiponectin amino acid sequence
```

<400> SEQUENCE: 22

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 23
<211> LENGTH: 423
<212> TYPE: DNA
<213> ORGANISM: Homo sapiens
<220> FEATURE:
<221> NAME/KEY: misc_feature
<223> OTHER INFORMATION: human adiponectin globular domain

<400> SEQUENCE: 23
cctggagaag gtgcctatgt ataccgctca gcattcagtg tgggattgga gacttacgtt    60
actatcccca acatgcccat tcgctttacc aagatcttct acaatcagca aaaccactat   120
gatggctcca ctggtaaatt ccactgcaac attcctgggc tgtactactt tgcctaccac   180
atcacagtct atatgaagga tgtgaaggtc agcctcttca gaaggacaa ggctatgctc   240 ttcacctatg atcagtacca ggaaaataat gtggaccagg cctccggctc tgtgctcctg   300
catctggagg tgggcgacca agtctggctc caggtgtatg gggaaggaga gcgtaatgga   360
ctctatgctg ataatgacaa tgactccacc ttcacaggct tcttctcta ccatgacacc   420 aac                                                                  423

```
<210> SEQ ID NO 24
<211> LENGTH: 141
<212> TYPE: PRT
<213> ORGANISM: Homo sapiens
<220> FEATURE:
<221> NAME/KEY: MISC_FEATURE
<223> OTHER INFORMATION: human adiponectin globular domain

<400> SEQUENCE: 24

Pro Gly Glu Gly Ala Tyr Val Tyr Arg Ser Ala Phe Ser Val Gly Leu
1               5                   10                  15

Glu Thr Tyr Val Thr Ile Pro Asn Met Pro Ile Arg Phe Thr Lys Ile
            20                  25                  30

Phe Tyr Asn Gln Gln Asn His Tyr Asp Gly Ser Thr Gly Lys Phe His
        35                  40                  45

Cys Asn Ile Pro Gly Leu Tyr Tyr Phe Ala Tyr His Ile Thr Val Tyr
    50                  55                  60

Met Lys Asp Val Lys Val Ser Leu Phe Lys Lys Asp Lys Ala Met Leu
65                  70                  75                  80

Phe Thr Tyr Asp Gln Tyr Gln Glu Asn Asn Val Asp Gln Ala Ser Gly
                85                  90                  95

Ser Val Leu Leu His Leu Glu Val Gly Asp Gln Val Trp Leu Gln Val
            100                 105                 110

Tyr Gly Glu Gly Glu Arg Asn Gly Leu Tyr Ala Asp Asn Asp Asn Asp
        115                 120                 125

Ser Thr Phe Thr Gly Phe Leu Leu Tyr His Asp Thr Asn
    130                 135                 140
```

METHOD FOR TREATING AND/OR PREVENTING NEURODEGENERATIVE DISEASE BY ADIPONECTIN RECEPTOR AGONIST

CROSS-REFERENCE TO PRIOR APPLICATION

This application claims priority to Japanese Patent Application No. 2011-274797, filed Dec. 15, 2011, the entire contents of which being hereby incorporated herein by reference.

TECHNICAL FIELD

The present invention relates to a method for treating and/or preventing neurodegenerative diseases including synucleinopathy. Particularly, the method of the present invention for treating and/or preventing neurodegenerative diseases, includes a step of administering an effective dose of an adiponectin receptor agonist and/or a compound inducing the corresponding agonist.

BACKGROUND

Neurodegenerative diseases are progressive diseases in which neuronal cells in the central nervous system gradually degenerate and die thereby. Among neurodegenerative diseases, it is known that abnormal accumulation of α (alpha)-synuclein occurs in synucleinopathies including Parkinson disease (PD), dementia with Lewy bodies (DLB), multiple system atrophy and the like. Further, it is known that abnormal accumulation of amyloid-β (beta)-protein and tau occurs in Alzheimer disease (AD). Furthermore, it is also known that abnormal accumulation of tau occurs in progressive supranuclear palsy, corticobasal degeneration and Pick's disease. Here, it has been elucidated that since genetic abnormalities in these proteins also cause familial neurodegenerative diseases, abnormal aggregation/accumulation of these proteins in the neuronal cells of the central nervous system leads to acquisition of neurotoxicity, i.e., mechanisms causing neuronal cell death or the like have mainly resulted in pathologies of neurodegenerative diseases.

Further, neurodegenerative diseases including Alzheimer disease and tau disease are caused by phosphorylated tau. Tau protein plays a role as a hinge between tubulins by binding to microtubules serving as structural proteins of neuronal cells, and has an ability to promote polymerization of tubulins into microtubules. When phosphorylated, tau protein loses the microtubule-binding ability, thus causing a collapse of normal cytoskeleton. Further, the phosphorylated tau protein causes neurodegeneration involving neurofibrillary tangle, accompanied with forming Paired Helical filaments (PHF). With regard to Alzheimer disease (AD), abnormal accumulation of amyloid-β (beta)-protein and tau is mainly observed. Further, accumulation of α (alpha)-synuclein is also observed in the brains of a large number of AD patients. Particularly, with regard to the ceruleus nuclei and amygdalae of the AD patients, it is known that Lewy bodies composed of α (alpha)-synuclein or the like and neurofibrillary tangle caused by tau protein colocalize in an identical neuronal cell. Further, phosphorylated tau and α (alpha)-synuclein exist in an identical location of a halo section of a brainstem-type Lewy body, and are assumed to together promote formation of neurofibrillary tangle. In fact, since AD is likely to be complicated by PD, and PD is likely to be complicated by AD, it is assumed that AD and PD are associated with each other at the molecular level.

PRIOR ART DOCUMENT

Nonpatent Document

Nonpatent document 1: Hashimoto M, Masliah E. Brain Pathol. 9(4): 707-20. (1999)

SUMMARY OF THE INVENTION

Problem to be Solved by the Invention

Among neurodegenerative diseases, those involving abnormal accumulation of α (alpha)-synuclein are referred to as synucleinopathies. Parkinson disease is the second most commonly observed neurodegenerative disease after Alzheimer disease. Dementia with Lewy bodies (DLB) is a cause of the third most commonly observed dementia after Alzheimer disease and cerebrovascular diseases. Currently, there exists no causal therapy for synucleinopathy. Here, serious social problems imposed thereby include: nursing care-related heavy burdens on family members; heavy burdens on nursing-care facilities; and enormous amounts of medical expenses. Accordingly, it is required that an effective method for treating synucleinopathy be developed.

Since neurodegenerative diseases are also considered as age-related diseases, exercises and calorie restriction are known to be effective in preventing neurodegenerative diseases as is the case in age-related diseases such as diabetes and arteriosclerosis. The inventors of the present invention have been focusing on adiponectin known as an antidiabetic factor and an antiatherogenic factor, and studying a role(s) of adiponectin against neurodegenerative diseases. Here, the inventors discovered that adiponectin suppressed aggregation of α (alpha)-synuclein, tau phosphorylation and a decrease in proteasomal activity. That is, the present invention was made based on the aforementioned findings.

Means to Solve the Problem

The present invention provides a composition for treatment and/or prevention of neurodegenerative diseases, the composition containing an adiponectin receptor agonist and/or a compound inducing the corresponding agonist.

In the composition of the present invention for treatment and/or prevention of neurodegenerative diseases, the adiponectin receptor agonist and/or the compound inducing the corresponding agonist may be at least one selected from a group consisting of: adiponectin protein; globular adiponectin protein; a compound inducing expression of adiponectin protein; and a compound inducing expression of globular adiponectin protein.

The present invention provides a pharmaceutical composition for suppression of α (alpha)-synuclein aggregation, tau phosphorylation and/or a decrease in proteasomal activity, the pharmaceutical composition containing the adiponectin receptor agonist and/or the compound inducing the corresponding agonist.

In the pharmaceutical composition of the present invention for suppression of α (alpha)-synuclein aggregation, tau phosphorylation and/or a decrease in proteasomal activity, the adiponectin receptor agonist and/or the compound inducing the corresponding agonist may be at least one selected from the group consisting of: adiponectin protein; globular adiponectin protein; a compound inducing expression of adiponectin protein; and a compound inducing expression of globular adiponectin protein.

The pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, may contain human adiponectin protein, and the aforementioned globular adiponectin protein may be a human globular adiponectin protein.

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned human adiponectin protein may be selected from a group consisting of: (1) a protein consisting of an amino acid sequence encoded by a polynucleotide consisting of a nucleotide sequence of SEQ. No. 21; (2) a protein that consists of an amino acid sequence encoded by a polynucleotide consisting of a nucleotide sequence having homology of not less than 80% with the nucleotide sequence of SEQ. No. 21, and has a property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 21 under a stringent condition, and has the property of suppressing human α (alpha)-synuclein aggregation, tau phosphorylation and/or a decrease in proteasomal activity in neuronal cells; (4) a human adiponectin protein consisting of an amino acid sequence of SEQ. No. 22; (5) a protein that consists of an amino acid sequence obtained by having one or several amino acid residues deleted from, added to or substituted in the amino acid sequence of SEQ. No. 22, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned human globular adiponectin protein may be selected from a group consisting of: (1) a protein consisting of an amino acid sequence encoded by a polynucleotide consisting of a nucleotide sequence of SEQ. No. 23; (2) a protein that consists of an amino acid sequence encoded by a polynucleotide consisting of a nucleotide sequence having homology of not less than 80% with the nucleotide sequence of SEQ. No. 23, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 23 under a stringent condition, and has the property of suppressing human α (alpha)-synuclein aggregation, tau phosphorylation and/or a decrease in proteasomal activity in neuronal cells; (4) a human globular adiponectin protein consisting of an amino acid sequence of SEQ. No. 24; (5) a protein that consists of an amino acid sequence obtained by having one or several amino acid residues deleted from, added to or substituted in the amino acid sequence of SEQ. No. 24, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned compound inducing expression of adiponectin may contain a polynucleotide encoding at least one protein selected from the group consisting of: (1) the protein consisting of the amino acid sequence encoded by the polynucleotide consisting of the nucleotide sequence of SEQ. No. 21; (2) a protein that consists of an amino acid sequence encoded by a polynucleotide consisting of a nucleotide sequence having homology of not less than 80% with the nucleotide sequence of SEQ. No. 21, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 21 under a stringent condition, and has the property of suppressing human α (alpha)-synuclein aggregation, tau phosphorylation and/or a decrease in proteasomal activity in neuronal cells; (4) the human adiponectin protein consisting of the amino acid sequence of SEQ. No. 22; (5) a protein that consists of an amino acid sequence obtained by having one or several amino acid residues deleted from, added to or substituted in the amino acid sequence of SEQ. No. 22, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned compound inducing expression of globular adiponectin may contain a polynucleotide encoding at least one protein selected from the group consisting of: (1) the protein consisting of the amino acid sequence encoded by the polynucleotide consisting of the nucleotide sequence of SEQ. No. 23; (2) a protein that consists of an amino acid sequence encoded by a polynucleotide consisting of a nucleotide sequence having homology of not less than 80% with the nucleotide sequence of SEQ. No. 23, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 23 under a stringent condition, and has the property of suppressing human α (alpha)-synuclein aggregation, tau phosphorylation and/or a decrease in proteasomal activity in neuronal cells; (4) the human globular adiponectin protein consisting of the amino acid sequence of SEQ. No. 24; (5) a protein that consists of an amino acid sequence obtained by having one or several amino acid residues deleted from, added to or substituted in the amino acid sequence of SEQ. No. 24, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned compound inducing expression of adiponectin may be a recombinant vector containing a polynucleotide encoding at least one protein selected from the group consisting of: (1) the protein consisting of the amino acid sequence encoded by the polynucleotide consisting of the nucleotide sequence of SEQ. No. 21; (2) a protein that consists of an amino acid sequence encoded by a polynucleotide consisting of a nucleotide sequence having homology of not less than 80% with the nucleotide sequence of SEQ. No. 21, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 21 under a stringent condition, and has the property of suppressing human α (alpha)-synuclein aggregation, tau phosphorylation and/or a decrease in proteasomal activity in neuronal cells; (4) the human adiponectin protein consisting of the amino acid sequence of SEQ. No. 22; (5) a protein that consists of an amino acid sequence obtained by having one or several amino acid residues deleted from, added to or substituted in the amino acid sequence of SEQ. No. 22, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned compound inducing expression of globular adiponectin may be a recombinant vector containing a polynucleotide encoding at least one protein selected from the group consisting of: (1) the protein consisting of the amino acid sequence encoded by the polynucleotide consisting of the nucleotide sequence of SEQ. No. 23; (2) a protein that consists of an amino acid sequence encoded by a polynucleotide consisting of a nucleotide sequence having homology of not less than 80% with the nucleotide sequence of SEQ. No. 23, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 23 under a stringent condition, and has the property of suppressing human α (alpha)-synuclein aggregation, tau phosphorylation and/or a decrease in proteasomal activity in neuronal cells; (4) the human globular adiponectin protein consisting of the amino acid sequence of SEQ. No. 24; (5) a protein that consists of an amino acid sequence obtained by having one or several amino acid residues deleted from, added to or substituted in the amino acid sequence of SEQ. No. 24, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

In the pharmaceutical composition of the present invention for treatment and/or prevention of neurodegenerative diseases and/or the pharmaceutical composition of the present invention for suppression of α (alpha)-synuclein aggregation, tau phosphorylation and/or a decrease in proteasomal activity, the aforementioned compound inducing expression of adiponectin may be a peroxisome proliferator-activated receptor (PPAR)-γ (gamma) agonist.

The present invention provides a method for treating and/or preventing neurodegenerative diseases. The method of the present invention includes a step of administering an effective dose of an adiponectin receptor agonist and/or a compound inducing the corresponding agonist.

With regard to the method of the present invention, the adiponectin receptor agonist and/or the compound inducing the corresponding agonist may be at least one selected from the group consisting of: adiponectin protein; globular adiponectin protein; a compound inducing expression of adiponectin protein; and a compound inducing expression of globular adiponectin protein.

The present invention provides a method for suppressing α (alpha)-synuclein aggregation, tau phosphorylation and/or a decrease in proteasomal activity. The method of the present invention includes a step of administering an effective dose of an adiponectin receptor agonist and/or a compound inducing the corresponding agonist, the adiponectin receptor agonist and/or the compound inducing the corresponding agonist being at least one selected from the group consisting of: adiponectin protein; globular adiponectin protein; a compound inducing expression of adiponectin protein; and a compound inducing expression of globular adiponectin protein.

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned adiponectin protein may be a human adiponectin protein, and the aforementioned globular adiponectin protein may be a human globular adiponectin protein.

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned human adiponectin protein may be selected from the group consisting of: (1) the protein consisting of the amino acid sequence encoded by the polynucleotide consisting of the nucleotide sequence of SEQ. No. 21; (2) a protein that consists of an amino acid sequence encoded by a polynucleotide consisting of a nucleotide sequence having homology of not less than 80% with the nucleotide sequence of SEQ. No. 21, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 21 under a stringent condition, and has the property of suppressing human α (alpha)-synuclein aggregation, tau phosphorylation and/or a decrease in proteasomal activity in neuronal cells; (4) the human adiponectin protein consisting of the amino acid sequence of SEQ. No. 22; (5) a protein that consists of an amino acid sequence obtained by having one or several amino acid residues deleted from, added to or substituted in the amino acid sequence of SEQ. No. 22, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned human globular adiponectin protein may be selected from the group consisting of: (1) the protein consisting of the amino acid sequence encoded by the polynucleotide consisting of the nucleotide sequence of SEQ. No. 23; (2) a protein that consists of an amino acid sequence encoded by a polynucleotide consisting of a nucleotide sequence having homology of not less than 80% with the nucleotide sequence of SEQ. No. 23, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 23 under a stringent condition, and has the property of suppressing human α (alpha)-synuclein aggregation, tau phosphorylation and/or a decrease in proteasomal activity in neuronal cells; (4) the human globular adiponectin protein consisting of the amino acid sequence of SEQ. No. 24; (5) a protein that consists of an amino acid sequence obtained by having one or several amino acid residues deleted from, added to or substituted in the amino acid sequence of SEQ. No. 24, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned compound inducing expression of adiponectin may contain a polynucleotide encoding at least one protein selected from the group consisting of: (1) the protein consisting of the amino acid sequence encoded by the polynucleotide consisting of the nucleotide sequence of SEQ. No. 21; (2) a protein that consists of an amino acid sequence encoded by a polynucleotide consisting of a nucleotide sequence having homology of not less than 80% with the nucleotide sequence of SEQ. No. 21, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 21 under a stringent condition, and has the property of suppressing human α (alpha)-synuclein aggregation, tau phosphorylation and/or a decrease in proteasomal activity in neuronal cells; (4) the human adiponectin protein consisting of the amino acid sequence of SEQ. No. 22; (5) a protein that consists of an amino acid sequence obtained by having one or several amino acid residues deleted from, added to or substituted in the amino acid sequence of SEQ. No. 22, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned compound inducing expression of globular adiponectin may contain a polynucleotide encoding at least one protein selected from the group consisting of: (1) the protein consisting of the amino acid sequence encoded by the polynucleotide consisting of the nucleotide sequence of SEQ. No. 23; (2) a protein that consists of an amino acid sequence encoded by a polynucleotide consisting of a nucleotide sequence having homology of not less than 80% with the nucleotide sequence of SEQ. No. 23, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 23 under a stringent condition, and has the property of suppressing human α (alpha)-synuclein aggregation, tau phosphorylation and/or a decrease in proteasomal activity in neuronal cells; (4) the human globular adiponectin protein consisting of the amino acid sequence of SEQ. No. 24; (5) a protein that consists of an amino acid sequence obtained by having one or several amino acid residues deleted from, added to or substituted in the amino acid sequence of SEQ. No. 24, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned compound inducing expression of adiponectin may be a recombinant vector containing a polynucleotide encoding at least one protein selected from the group consisting of: (1) the protein consisting of the amino acid sequence encoded by the polynucleotide consisting of the nucleotide sequence of SEQ. No. 21; (2) a protein that consists of an amino acid sequence encoded by a polynucleotide consisting of a nucleotide sequence having homology of not less than 80% with the nucleotide sequence of SEQ. No. 21, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 21 under a stringent condition, and has the property of suppressing human α (alpha)-synuclein aggregation, tau phosphorylation and/or a decrease in proteasomal activity in neuronal cells; (4) the human adiponectin protein consisting of the amino acid sequence of SEQ. No. 22; (5) a protein that consists of an amino acid sequence obtained by having one or several amino acid residues deleted from, added to or substituted in the amino acid sequence of SEQ. No. 22, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned compound inducing expression of globular adiponectin may be a recombinant vector containing a polynucleotide encoding at least one protein selected from the group consisting of: (1) the protein consisting of the amino acid sequence encoded by the polynucleotide consisting of the nucleotide sequence of SEQ. No. 23; (2) a protein that consists of an amino acid sequence encoded by a polynucleotide consisting of a nucleotide sequence having homology of not less than 80% with the nucleotide sequence of SEQ. No. 23, and has the property of suppressing human α (alpha)-synuclein aggregation, tau phosphorylation and/or a decrease in proteasomal activity in neuronal cells; (3) a protein that consists of an amino acid sequence encoded by a polynucleotide hybridizable with the polynucleotide consisting of the nucleotide sequence of SEQ. No. 23 under a stringent condition, and has the property of suppressing human α (alpha)-synuclein aggregation, tau phosphorylation and/or a decrease in proteasomal activity in neuronal cells; (4) the human globular adiponectin protein consisting of the amino acid sequence of SEQ. No. 24; (5) a protein that consists of an amino acid sequence obtained by having one or several amino acid residues deleted from, added to or substituted in the amino acid sequence of SEQ. No. 24, and has the property of suppressing human α (alpha)-synuclein aggregation, tau phosphorylation and/or a decrease in proteasomal activity in neuronal cells; and (6) a fusion protein obtained by allowing a tag peptide for specific binding to bind to any of the proteins of (1) through (5).

With regard to the method of the present invention for treating and/or preventing neurodegenerative diseases and/or the method of the present invention for suppressing α (alpha)-synuclein aggregation, tau phosphorylation and/or a decrease in proteasomal activity, the aforementioned compound inducing expression of adiponectin may be a peroxisome proliferator-activated receptor (PPAR)-γ (gamma) agonist.

With regard to the method of the present invention for treating and/or preventing neurodegenerative diseases and/or the method of the present invention for suppressing α (alpha)-synuclein aggregation, tau phosphorylation and/or a decrease in proteasomal activity, the peroxisome proliferator-activated receptor (PPAR)-γ (gamma) agonist may be a pioglitazone hydrochloride.

The present invention provides a screening method for a compound that inhibits and/or improves neurodegeneration by suppressing α (alpha)-synuclein aggregation, aggregation of phosphorylated tau and/or a decrease in proteasomal activity, by adiponectin.

The screening method of the present invention may include: (a) a step of preparing biological materials expressing α (alpha)-synuclein; (b) a step of bringing the biological materials into contact with test compounds; (c) a step of determining a measurement value of at least one object that is derived from the biological materials and selected from a group consisting of an amount of protein and/or mRNA of adiponectin, an amount of protein and/or mRNA of adiponectin receptor, an amount of phosphorylated tau, an amount and/or activity of kinase, an amount of α (alpha)-synuclein aggregates, an amount of adiponectin and α (alpha)-synuclein aggregates, and proteasomal activity; and (d) a step of comparing the effects of the test compounds based on the measurement value determined.

The present invention may include: (a) a step of preparing α (alpha)-synuclein expressing cells; (b) a step of performing incubation by adding the test compounds to the aforementioned cells; (c) a step of determining a measurement value of at least one object selected from a group consisting of the amount of protein and/or mRNA of adiponectin, the amount and/or activity of kinase, the amount of α (alpha)-synuclein aggregates, the amount of adiponectin and α (alpha)-synuclein aggregates, and proteasomal activity; and (d) the step of comparing the effects of the test compounds based on the measurement value determined.

With regard to the screening method of the present invention, the aforementioned step (a) may be a step of culturing the α (alpha)-synuclein expressing cells in the presence of a proteasome inhibitor.

The screening method of the present invention may include a step of introducing siRNA of adiponectin and/or adiponectin receptor into the cells prepared in the step (a).

The screening method of the present invention may include the step of introducing siRNA of adiponectin and/or adiponectin receptor into the cells prepared in the step (a).

With regard to the screening method of the present invention, the kinase in the step (c) may be at least one selected from a group consisting of: AMPK; phosphorylated AMPK; p38 MAPK; phosphorylated p38 MAPK; GSK-3β (beta); and phosphorylated GSK-3β (beta).

The screening method of the present invention may include: (a) a step of incubating the test compounds and brain samples removed from a transgenic animal neuron-specifically expressing human α (alpha)-synuclein; (b) a step of determining a measurement value of at least one object selected from a group consisting of an amount of protein and/or mRNA of adiponectin, an amount of protein and/or mRNA of adiponectin receptor, an amount of phosphorylated tau, an amount and/or activity of kinase, an amount of α (alpha)-synuclein aggregates, an amount of adiponectin and α (alpha)-synuclein aggregates, and proteasomal activity; and (c) the step of comparing the effects of the test compounds based on the measurement value determined.

The screening method of the present invention may include: (a) a step of administering the test compounds to the transgenic animal neuron-specifically expressing α (alpha)-synuclein; (b) the step of determining a measurement value of at least one object that is derived from the brain samples of the transgenic animal and selected from a group consisting of the amount of protein and/or mRNA of adiponectin, the amount of protein and/or mRNA of adiponectin receptor, the amount of phosphorylated tau, the amount and/or activity of kinase, the amount of α (alpha)-synuclein aggregates, the amount of adiponectin and α (alpha)-synuclein aggregates, and proteasomal activity; and (c) the step of comparing the effects of the test compounds based on the measurement value determined.

In this specification, "protein," "peptide," "oligopeptide" or "polypeptide" refers to a compound in which two or more amino acids are linked together by peptide bonds. "Protein," "peptide," "oligopeptide" or "polypeptide" may be modified by: alkyl group including methyl group; phosphate group; and/or sugar chains. "Protein," "peptide," "oligopeptide" or "polypeptide" may also be modified through ester bond and/or covalent bond. Further, through either covalent bond or non-covalent bond, "protein," "peptide," "oligopeptide" or "polypeptide" may bind to or be associated with: metal ions, coenzymes or allosteric ligands (or other atoms, ions or atomic groups); other "protein," "peptide," "oligopeptide" or "polypeptide"; biological polymers such as sugars, lipids, nucleic acids or the like; or synthetic polymers such as polystyrene, polyethylene, polyvinyl, polyester or the like.

Adiponectin is a gene product massively expressed in adipocytes cloned in accordance with Maeda, K. et al., (Biochem. Biophys. Res. Commun. 221:286 (1996)), and serves to suppress or inhibit differentiation of adipocytes. mRNA of adiponectin is not detected in normal brains by northern blotting. When administered to cerebral ventricles, there has been mainly observed an effect of reducing body weight by stimulating energy consumption. Adiponectin causes the effect of the present invention of treating and/or preventing neurodegenerative diseases, due to: its property of suppressing or reducing α (alpha)-synuclein aggregation and/or tau phosphorylation; and/or its property of suppressing a decrease in proteasomal activity. A nucleotide sequence in the coding region of human adiponectin is shown in SEQ. No. 21 of a sequence listing attached to this specification, and an amino acid sequence in the coding region of human adiponectin is shown in SEQ. No. 22 of the sequence listing attached to this specification. In the present invention, human adiponectin may also be an equivalent thereof, i.e., a protein consisting of an amino acid sequence significantly analogous to that of human adiponectin, and having the activity of suppressing human α (alpha)-synuclein aggregation, tau phosphorylation and/or a decrease in proteasomal activity in neuronal cells, the activity being the activity of adiponectin of the present invention.

Globular adiponectin is one of the isoforms of adiponectin whose N-terminal collagen-like domain has been cut by protease, and functions as an agonist with respect to adiponectin receptor.

In the present invention, adiponectin receptor agonist refers to a compound that exhibits functions similar to those of adiponectin by interacting with adiponectin receptor. Adiponectin receptor agonist of the present invention may be the aforementioned adiponectin, recombinant adiponectin, the aforementioned globular adiponectin or recombinant globular adiponectin.

There exist two kinds of adiponectin receptor (Adipo R) which are Adipo R1 and Adipo R2 functioning as receptors of globular adiponectin and full-length adiponectin. The aforementioned receptors are known to mediate: activation of a signal transmission molecules including AMPK, PPAR-α (alpha) and p38 MAPK; oxidation of fatty acids; and an increase in ingestion of glucose.

In the present invention, by interacting with adiponectin receptor, adiponectin receptor agonist serves to: induce and/or activate a kinase such as AMPK, p38 MAPK and GSK-3β (beta) that contribute to intracellular signaling; increase the amounts of phosphorylated AMPK, phosphorylated p38 MAPK and phosphorylated GSK-3β (beta); and suppress tau phosphorylation, aggregation of phosphorylated tau, α (alpha)-synuclein aggregation and/or formation of aggregation of tau and α (alpha)-synuclein.

In the present invention, compound inducing expression of adiponectin refers to a compound that induces expression of adiponectin when orally or parenterally administered to cultured cells or individuals such as human or test animals. Induction of adiponectin expression refers to: an incident in which the amount of adiponectin increases in the cells where adiponectin is produced; and/or an incident in which adiponectin is secreted from the adiponectin-producing cells. The aforementioned compound inducing expression of adiponectin may contain cDNA encoding adiponectin or an equivalent thereof. Further, the compound inducing expression of adiponectin may be a recombinant vector containing cDNA encoding adiponectin or an equivalent thereof. The compound inducing expression of adiponectin may be, but not limited to: KLF9 disclosed in WO2005/094866; an acylamido compound disclosed in Japanese Unexamined Patent Application Publication No. 2008-10594; PPAR-γ (gamma) agonist (e.g., pioglitazone hydrochloride) disclosed in Japanese Unexamined Patent Application Publication No. 2008-195630; porphyran (or a salt thereof) disclosed in Japanese Unexamined Patent Application Publication No. 2011-148748; or an extract extracted from a hypsizygus tessellatus disclosed in Japanese Unexamined Patent Application Publication No. 2011-236236. That is, the compound inducing expression of adiponectin may be any compound known to induce adiponectin expression before the application of the present invention. Moreover, the pharmaceutical composition of the present invention for treatment and/or prevention of synucleinopathies, may contain any compound promoting passage of the compound inducing adiponectin expression through blood-brain barriers.

In the present invention, a compound inducing expression of globular adiponectin refers to a compound that induces expression of globular adiponectin when orally or parenterally administered to cultured cells or individuals such as human or test animals. Induction of globular adiponectin expression refers to: a phenomenon in which the amount of globular adiponectin increases in the cells where globular adiponectin is produced; and/or a phenomenon in which globular adiponectin is secreted from the globular adiponectin-producing cells. The aforementioned compound inducing expression of globular adiponectin may contain cDNA encoding globular adiponectin or an equivalent thereof. Further, the compound inducing expression of globular adiponectin may be a recombinant vector containing cDNA encoding globular adiponectin or an equivalent thereof. The compound inducing expression of globular adiponectin may be, but not limited to: KLF9 disclosed in WO2005/094866; the acylamido compound disclosed in Japanese Unexamined Patent Application Publication No. 2008-10594; PPAR-γ (gamma) agonist (e.g., pioglitazone hydrochloride) disclosed in Japanese Unexamined Patent Application Publication No. 2008-195630; porphyran (or a salt thereof) disclosed in Japanese Unexamined Patent Application Publication No. 2011-148748; or the extract extracted from the hypsizygus tessellatus disclosed in Japanese Unexamined Patent Application Publication No. 2011-236236. Moreover, the pharmaceutical composition of the present invention for treatment and/or prevention of synucleinopathies, may contain any compound promoting passage of the compound inducing globular adiponectin expression through blood-brain barriers.

The composition of the present invention may further contain one or more than one kind of pharmaceutically allowable additive(s), as long as without reducing the effect of suppressing α (alpha)-synuclein aggregation, tau phosphorylation and/or a decrease in proteasomal activity in neuronal cells, that is caused by adiponectin, the compound inducing expression of adiponectin, globular adiponectin and/or the compound inducing expression of globular adiponectin. The aforementioned additive may be, but not limited to: a binding agent; a lubricating agent; a disintegrating agent; a solubilizing agent; a buffering agent; a coloring agent; a flavoring agent; an edulcorant; a preservative agent; a stabilizing agent; or other pharmaceutical additives known to those skilled in the art.

In the present invention, an effective dose refers to a dosage amount allowing the effect of the composition of the present invention to be achieved in a subject without harming the health of the corresponding subject to which the composition is administered. The effective dose may be determined in view of the subject's body weight, age, sex, genotype, medical condition or the like.

A dosage form of the composition of the present invention is not particularly limited, as long as the effect of suppressing α (alpha)-synuclein aggregation, tau phosphorylation and/or a decrease in proteasomal activity in neuronal cells is not reduced, the effect being caused by adiponectin, the compound inducing expression of adiponectin, globular adiponectin and/or the compound inducing expression of globular adiponectin. The dosage form of the composition of the present invention may, for example, be a nasal preparation such as a nasal spray or the like.

The composition of the present invention is preferably manufactured in accordance with a manufacture/quality management standard for pharmaceutical products and quasi-pharmaceutical products (good manufacturing practice, GMP).

With regard to a delivery of the compound of the present invention, there can be employed a delivery system that is known to those skilled in the art and is capable of quantitatively, spatially and temporally controlling a biodistribution of adiponectin, the compound inducing expression of adiponectin, globular adiponectin and/or the compound inducing expression of globular adiponectin.

In the present invention, neurodegenerative diseases refer to progressive diseases in which neuronal cells in the central nervous system gradually degenerate due to abnormal accumulation of protein causing dysfunction or neuronal death. The aforementioned neurodegenerative diseases include, but are not limited to: Parkinson disease; dementia with Lewy bodies; Alzheimer disease; progressive supranuclear palsy; corticobasal degeneration; Pick's disease; and multiple system atrophy. Neurodegenerative diseases in the present invention may be synucleinopathies involving abnormal accumulation of α (alpha)-synuclein.

In the present invention, adiponectin interacts with α (alpha)-synuclein in neuronal cells, thereby suppressing or reducing α (alpha)-synuclein aggregation and/or tau phosphorylation or improving a decrease in proteasomal activity, thus inhibiting accumulation of α (alpha)-synuclein. However, as shown in the examples of this specification, it is suggested that a direct protein-protein interaction takes place between adiponectin and α (alpha)-synuclein. Accordingly, the present invention may also cause the effect of treating and/or preventing synucleinopathies by suppressing or reducing extracellular formation of α (alpha)-synuclein aggregates.

Nucleotide sequence homology in this specification is obtained as follows. That is, a nucleotide sequence of the present invention and a nucleotide sequence for comparison are aligned such that a largest number of identical portions are identified. Specifically, nucleotide sequence homology in the present invention is a quotient (expressed as percentage) obtained by dividing the number of nucleotides in the identical portions between the nucleotide sequences by a total number of nucleotides in the nucleotide sequence of the present invention. Similarly, amino acid sequence homology in this specification is obtained as follows. That is, an amino acid sequence of the present invention and an amino acid sequence for comparison are aligned such that a largest number of amino acid residues in identical portions are identified. Specifically, amino acid sequence homology in the present invention is a quotient (expressed as percentage) obtained by dividing a total number of the amino acid residues in the identical portions between the amino acid sequences by a total number of the amino acid residues in the amino acid sequence of the present invention. In the present invention, nucleotide sequence homology and amino acid sequence homology can be calculated using CLUSTALW which is a sequence alignment program known to those skilled in the art.

In this specification, a "stringent condition" refers to the following experimental condition under which southern blotting known to those skilled in the art is performed. A polynucleotide consisting of a nucleotide sequence for comparison is subjected to agarose electrophoresis to form bands, followed by being immobilized on a nitrocellulose filter or an other solid phase through capillary action or electrophoresis. Preliminary washing is then performed using a solution of 6×SSC and 0.2% SDS. Using the solution of 6×SSC and 0.2% SDS, Hybridization is then performed overnight at 65° C. between: a probe obtained by labeling a polynucleotide consisting of a nucleotide sequence of the present invention with a radioisotope or an other labeling substance; and the polynucleotide for comparison that has been immobilized on the solid phase. Later, the solid phase is washed twice for 30 min at a time in a solution of 1×SSC and 0.1% SDS at 65° C., followed by being washed twice for 30 min at a time in a solution of 0.2×SSC and 0.1% SDS at 65° C. In the end, an amount of probe remaining on the solid phase is determined by measuring the quantity of the aforementioned labeling substance. In this specification, hybridization performed under a "stringent condition" refers to hybridization in which the amount of the probe remaining on the solid phase used to immobilize a polynucleotide consisting of a nucleotide sequence for comparison is at least 25%, preferably at least 50%, more preferably at least 75% of an amount of a probe remaining on a solid phase used in a positive control experiment to immobilize a polynucleotide consisting of a nucleotide sequence of the present invention.

The fusion protein in the present invention refers to a protein obtained by allowing a tag peptide for specific binding to bind to amino terminal end or carboxyl terminal end of any of the proteins of (1) through (5).

The tag peptide for specific binding in the present invention refers to a polypeptide specifically binding to, for example: other proteins; polysaccharides; glycolipids; nucleic acids; derivatives of these substances; and resins, such that detection, separation or purification of the proteins expressed is made easier when preparing any of the proteins of (1) through (5). A ligand bound to a tag for specific binding may be immobilized by a solid support even when dissolved in a water solution and forming a free state thereby. Here, since the fusion protein of the present invention specifically binds to the ligand immobilized by the solid support, other components in the expression system can be washed and removed. Later, the fusion protein can be collected from the solid support through separation, by, for example, adding ligands in the free state and changing pH, ionic strength as well as other conditions. The tag for specific binding in the present invention may be, but not limited to: His tag; myc tag; HA tag; intein tag, MBP; GST; or other polypeptides analogous thereto. The tag for specific binding in the present invention may have any kind of amino acid sequence, as long as the fusion protein is allowed to preserve the activity to suppress human α (alpha)-synuclein aggregation and/or tau phosphorylation in neuronal cells.

In this specification, a "recombinant vector" is a vector used to express a protein having a desired function in a host organism, the vector containing a polynucleotide encoding the protein having the desired function.

In this specification, a "vector" may be, but not limited to: plasmid; virus; phage; or cosmid and the like, all of which serves to replicate and express a protein having a desired function in a host organism, by introducing into the host organism a polynucleotide encoding the protein having the desired function. Preferably, the "vector" may be plasmid.

The recombinant vector in the present invention may be manufactured by binding any vector to the polynucleotide encoding the protein of the present invention in accordance with genetic engineering procedures that employ restriction enzymes, DNA joining enzymes or the like and is known to those skilled in the art The aforementioned biological materials may be, but not limited to: cells, tissues and organs that are collected from living organisms of human and test animals; or cultured cells related thereto. The cultured cells may be, but not limited to: primary cultured cells of the cells collected from living organisms; sub-cultured cells thereof; cells differentiated from iPS cells, ectodermal stem cells or other multipotential stem cells; or cell lines. The cell line may be a B103 neuroblastoma cell. The aforementioned test animals include knockout animals and transgenic animals. Transgenic animals may be Thy-1-α (alpha)S transgenic mice (α (alpha)S tg mice). The biological materials can be prepared by standard methods known to those skilled in the art. Organism species from which the biological materials are obtained, include but are not limited to: human; monkey; mouse; rat; rabbit; hamster; goat; and pig. Human may be, but not limited to: a healthy subject; or a patient of neurodegenerative disease (e.g., Parkinson disease, dementia with Lewy bodies, multiple system atrophy, Alzheimer disease, progressive supranuclear palsy, corticobasal degeneration and Pick's disease). In the present invention, the biological materials are used in vitro, ex vivo or in vivo.

With regard to the screening method of the present invention, the test compounds include but are not limited to: compounds prepared from microorganisms, fungi, plants and animals; and compounds that are chemically-synthesized.

In the present invention, mRNA amount refers not only to an amount of a desired mRNA in cells, but also to transcription activity of a desired gene in the corresponding cells. The amount of the desired mRNA in the cells is measured by RT-PCR, northern blotting or any other methods involving solid-phase hybridization. A desired transcription activity in the aforementioned cells is typically measured by temporarily or permanently introducing into cultured cells a construct that allows a reporter protein to operate through an expression control region of a desired gene, the reporter protein being chloramphenicol acetyltransferase (CAT), β (beta)-galactosidase (Lac Z), luciferase (Luc), green fluorescent protein (GFP) or other reporter protein. In order to measure the amount of the desired mRNA in the aforementioned cells by RT-PCR, oligonucleotides consisting of the nucleotide sequences shown in the sequence listing may be used as a pair of primers.

In the present invention, the mRNA amount may be determined as a measurement value standardized by the number of the cells or the total amount of mRNA used for measurement. Alternatively, when inoculating the same number of cells in a plurality of identical containers such as wells, dishes, flasks or the like, the amount of desired mRNA in each container after culturing may be expressed as a measurement value based on the amount of desired mRNA in the cells to which the test compounds have not yet been added. Further, when inoculating the same number of cells in a plurality of identical containers such as wells, dishes, flasks or the like, the desired mRNA amount in the present invention may be standardized by an mRNA amount of a control gene in each container treated under the same condition. The control gene may be, but not limited to so-called house-keeping gene. In fact, the control gene can be found by a measure such as gene expression array chip analysis or the like. In the present invention, house-keeping gene may be, but not limited to: 28 SrRNA; 18 SrRNA; glucose-6-phosphate dehydrogenase (G6PD); glyceraldehyde-3-phosphate dehydrogenase (GAPDH); β (beta)-actin; or cyclophilin A. In order to measure an mRNA amount of cyclophilin A in the cells through RT-PCR, oligonucleotides consisting of the nucleotide sequences shown in SEQ. No. 13 and SEQ. No. 14 may be used as a pair of primers. With regard to the screening method of the present invention, the effects of the test compounds may be compared using the aforementioned measurement value.

The desired mRNA may be, but not limited to: mature mRNA; splicing variant; or immature mRNA.

Solid-phase hybridization in the present invention may be, but not limited to hybridization to a gene expression array chip, other than northern blotting.

In the present invention, protein amount may be not only the amount of protein produced by cells, but also the amount of protein existing in the biological materials collected. An amount of a desired protein may be measured by, but not limited to ELISA, western blotting, immunoprecipitation, immunonephelometry or other methods. When performing the aforementioned methods, there may be employed antibodies specifically recognizing the desired protein. The antibodies may be either prepared through standard methods known to those skilled in the art, or obtained commercially.

In the present invention, protein amount may be determined as a measurement value standardized by the number of the cells or the total amount of protein at the time of measurement. Alternatively, when inoculating the same number of cells in a plurality of identical containers such as wells, dishes, flasks or the like, the amount of the desired protein in each container after culturing may be expressed as a measurement value based on the amount of the desired protein in the cells to which the test compounds have not yet been added. Further, when inoculating the same number of cells in a plurality of identical containers such as wells, dishes, flasks or the like, the amount of the desired protein in the present invention may be standardized by an amount of a control protein in each container treated under the same condition. The control protein is a protein encoded by so-called house-keeping. Particularly, the control protein may be, but not limited to, β (beta)-actin or γ (gamma)-tubulin. In order to measure the amount of the protein encoded by house-keeping gene by ELISA or the like, there may be employed antibodies specifically recognizing the aforementioned protein. With regard to the screening method of the present invention, the effects of the test compounds may be compared using the aforementioned measurement value.

In the present invention, amount of phosphorylated tau and/or kinase may be not only the amount of phosphorylated tau and/or kinase produced by cells, but also the amount of phosphorylated tau and/or kinase existing in the biological materials collected. An amount of desired phosphorylated tau and/or kinase may be measured by ELISA, western blotting, immunoprecipitation, immunonephelometry or other methods. When performing the aforementioned methods, there may be employed antibodies specifically recognizing the desired phosphorylated tau or kinase. The antibodies may be either prepared by standard methods known to those skilled in the art, or obtained commercially.

In the present invention, amount of phosphorylated tau and/or kinase may be determined as a measurement value standardized by the number of the cells or the total amount of protein at the time of measurement. Alternatively, when inoculating the same number of cells in a plurality of identical containers such as wells, dishes, flasks or the like, the amount of phosphorylated tau and/or kinase in each container after culturing may be expressed as a measurement value based on the amount of the desired phosphorylated tau and/or kinase in the cells to which the test compounds have not yet been added. Further, when inoculating the same number of cells in a plurality of identical containers such as wells, dishes, flasks or the like, the amount of the desired phosphorylated tau and/or kinase in the present invention may be standardized by an amount of a control phosphorylated protein in each container treated under the same condition. Particularly, the aforementioned kinase may be, but not limited to: AMPK; p38 MAPK; and/or GSK-3β (beta). With regard to the screening method of the present invention, the effects of the test compounds may be compared using the aforementioned measurement value.

In the present invention, kinase activity may be not only the activity of kinase produced by cells, but also the activity of kinase existing in the biological materials collected. Activity of a desired kinase may be measured by ELISA or other methods.

In the present invention, kinase activity may be determined as a measurement value standardized by the number of the cells or the total kinase activity at the time of measurement. Alternatively, when inoculating the same number of cells in a plurality of identical containers such as wells, dishes, flasks or the like, the activity of the desired kinase in each container after culturing may be expressed as a measurement value based on the activity of the desired kinase in the cells to which the test compounds have not yet been added. Further, when inoculating the same number of cells in a plurality of identical containers such as wells, dishes, flasks or the like, the activity of the desired kinase in the present invention may be standardized by the control of kinase activity in each container treated under the same condition. With regard to the screening method of the present invention, the effects of the test compounds may be compared using the aforementioned measurement value.

In the present invention, amount of aggregates may be not only the amount of aggregates produced by cells, but also the amount of aggregates existing in the biological materials collected. An amount of desired aggregates may be measured by ELISA, western blotting, immunoprecipitation, immunonephelometry or other methods, but not limited to these. When performing the aforementioned methods, there may be employed antibodies specifically recognizing the desired aggregates. The antibodies may be either prepared by standard methods known to those skilled in the art, or obtained commercially.

In the present invention, amount of aggregates may be determined as a measurement value standardized by the number of the cells or the total amount of aggregates at the time of measurement. Alternatively, when inoculating the same number of cells in a plurality of identical containers such as wells, dishes, flasks or the like, the amount of the desired aggregates in each container after culturing may be expressed as a measurement value based on the amount of the desired aggregates in the cells to which the test compounds have not yet been added. The aforementioned aggregates may be, but not limited to: α (alpha)-synuclein aggregates; or aggregates of adiponectin and α (alpha)-synuclein. With regard to the screening method of the present invention, the effects of the test compounds may be compared using the aforementioned measurement value.

In the present invention, proteasomal activity may be not only proteasomal activity of the cultured cells, but also that of the biological materials collected. The aforementioned proteasomal activity can be measured using a commercially available kit. Proteasome in the present invention may be 20S proteasome, 26S proteasome or the like.

In the present invention, proteasomal activity may be determined as a measurement value standardized by the number of the cells or the total proteasomal activity at the time of measurement. Alternatively, when inoculating the same number of cells in a plurality of identical containers such as wells, dishes, flasks or the like, a desired proteasomal activity in each container after culturing may be expressed as a measurement value based on the proteasomal activity in the cells to which the test compounds have not yet been added. With regard to the screening method of the present invention, the effects of the test compounds may be compared using the aforementioned measurement value.

With regard to the screening method of the present invention, there may be used siRNA of adiponectin, siRNA of adiponectin receptor and an adiponectin-receptor inhibitor. Further, with regard to the screening method of the present invention, screening conditions may be changed as follows. For example, while compounds other than the test compounds may be administered, there may also be changes in conditions for cell culture such as temperature, gas composition and gas partial pressure, and in conditions for breeding such as temperature, feeding procedure and light-dark period.

All the documents referred to in this specification are incorporated as the citations of the original documents.

MODE FOR CARRYING OUT THE INVENTION

Figure 1A:
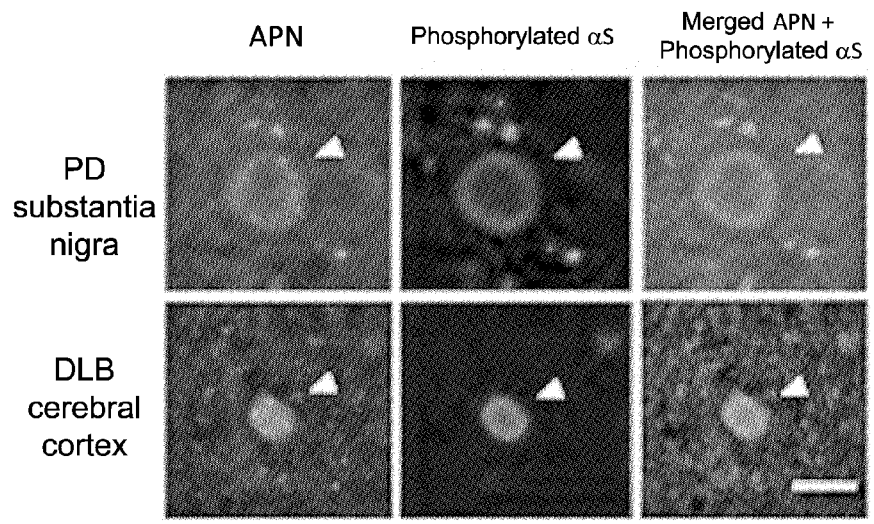
FIG. 1A is a series of confocal microscopic photographs of brain samples that were obtained from a PD patient and a DLB patient, and stained by immunohistochemical staining.

Examples of the present invention described below are intended only to exemplify the invention rather than to limit the scope thereof. The scope of the present invention is limited only by the description in claims. In fact, the present invention can be modified by addition, elimination and substitution of constituent features, without departing from the gist of the invention.

The following experiments were performed based on an approval of research ethics committee of Tokyo Metropolitan Institute of Medical Science (the former Tokyo Metropolitan Institute for Neuroscience) (approval number: 2302, approval date: 2011.4.1)

Further, the following experiments were performed in accordance with the guidelines of National Institutes of Health (NIH).

Experimental Example 1

Expression and Location of Adiponectin in Human Brain

1. Material and Method 1.1 Antibody

An anti-adiponectin C-terminus recognizing rabbit polyclonal antibody (Novus Biologicals, LLC), an anti-adiponectin N-terminus recognizing rabbit polyclonal antibody (Abcam plc.), an anti-adiponectin receptor 1 (AdipoR1) goat polyclonal antibody (Santa Cruz Biotechnology, Inc), an anti-α (alpha)-synuclein mouse monoclonal antibody (syn-1, Nippon Becton Dickinson Company, Ltd), an anti-phosphorylated α (alpha)-synuclein mouse monoclonal antibody (Wako Pure Chemical Industries, Ltd.) and an anti-β (beta)-actin mouse monoclonal antibody (C-15, Sigma-Aldrich Japan Inc.) were used as primary antibodies after being appropriately diluted.

With regard to fluorescence immunohistochemical staining, an Alexa Fluor 488 labeled anti-rabbit antibody and an Alexa Fluor 594 labeled anti-mouse antibody (Invitrogen, Life Technologies Japan Ltd.) were used as secondary antibodies after being appropriately diluted. As for western blotting, an HRP labeled anti-rabbit IgG antibody, an HRP labeled anti-goat IgG antibody and an HRP labeled anti-mouse IgG antibody (DAKO) were used as secondary antibodies after being appropriately diluted.

1.2 Autopsied Brain

Provided from Dr. Hiroyasu Akatsu in Fukushimura Brain Bank were: brain samples obtained from patients of sporadic Parkinson's disease (referred to as "PD" hereinafter); brain samples obtained from patients of sporadic dementia with Lewy bodies (referred to as "DLB" hereinafter); and brain samples obtained from healthy subjects. Diagnoses of PD and DLB were performed on the basis of diagnostic criteria of Calne, et al., (Ann Neurol. 32(Suppl): S125(1992)) and a report on DLB consortium (Mckeith et al., Neurology 65:1863(2005)). Autopsies of the aforementioned brain samples were performed two hours after death. Here, samples for western blotting were frozen for preservation at −80° C. As for samples used in fluorescence immunohistochemical staining, while the brain sample of the PD patient (midbrain substantia nigra) was immersion-fixed with 4% paraformaldehyde (PFA), the brain sample of the DLB patient (cingulate cortex) was immersion-fixed with methacarn fixing solution (methanol/chloroform/glacial acetic acid), followed by embedding the brain samples thus immersion-fixed in paraffin.

1.3 Fluorescence Immunohistochemical Staining

Fluorescence immunohistochemical staining was performed in a standard manner known to those skilled in the art. Briefly, the brain samples were embedded in paraffin, and then sliced into thin sections of a thickness of 4 µm. After deparaffinization, the thin sliced sections were immersed in 10 mM sodium citrate buffer (pH 6.0), followed by performing an epitope retrieval treatment (95° C., 10 min) using microwave (MW). After the epitope retrieval treatment, the thin sliced sections were subjected to blocking for 30_min, using 10% goat normal serum (Vector Laboratories, Inc.)/0.1% bovine serum albumin (BSA)/TBS (25 mM Tris-HCl (pH 7.5), 0.15 M NaCl). The thin sliced sections were then incubated overnight at 4° C. with the primary antibodies diluted with 0.1% bovine serum albumin (BSA)/TBS. After washing, the thin sliced sections were further incubated for an hour at room temperature with the Alexa Fluor labeled secondary antibodies diluted with 0.1% BSA/TBS. After embedding, the thin sliced sections were observed with a confocal laser scanning microscope (FV 1000, Olympus Corporation).

1.4 Extraction of Various Soluble Fractions and Detection by Western Blotting

Western blotting was performed in accordance with the method employed by Fujita et al. (Fujita et al., Nat. Commun. 1:110 (2010)). Each brain sample was homogenized in TBS before being centrifuged at 100,000×g, 4° C. for 30 min, thus allowing a supernatant to be collected as a TBS soluble fraction. TBS insoluble precipitates were dissolved in 1% SDS before being centrifuged at 100,000×g, thus allowing supernatants to be collected as SDS soluble fractions. An SDS insoluble precipitates were dissolved in 70% formic acid (FA) before being centrifuged at 20,000×g. Here, supernatants were collected as formic acid soluble fractions. The formic acid soluble fractions thus collected were then dried under a reduced pressure by means of a centrifugal thickener (TOMY SEIKO CO., LTD.), followed by dissolving the formic acid soluble fractions thus dried in 1×SDS sample buffer. Protein concentration of each fraction was measured using a BioRad Protein Assay reagent (Bio-Rad Laboratories, Inc.). Particularly, 10 tg per lane was dissolved in 1×SDS sample buffer containing 2-mercaptoethanol (2ME). In order to detect adiponectin, the samples were shaken for 30 min and then heated at 95° C. for 10 min. In other cases, the samples were simply heated at 95° C. for 10 min without being shaken. After performing SDS-PAGE (10-16%), proteins were transferred to a nitrocellulose membrane (GE Healthcare Japan Corporation). The nitrocellulose membrane was subjected to blocking for 30_min, using TBS to which 3% BSA/0.2% Tween 20 had been added. The nitrocellulose membrane thus treated was then incubated overnight at 4° C. with the primary antibodies diluted with TBS to which 3% BSA/0.2% Tween 20 had been added. Subsequently, the nitrocellulose membrane was washed using TBS to which 0.2% Tween 20 had been added, and then incubated with the secondary antibodies, thus allowing antigen-antibody complex to be detected by means of an ECL Plus kit (GE Healthcare Japan Corporation).

2 Result 2.1 Immunohistochemical Staining

FIG. 1A is a series of confocal microscopic photographs of the brain samples that had been obtained from the PD patient and the DLB patient and stained by immunohistochemical staining Shown in upper sections of the photographs of FIG. 1A are the primary antibodies that were used. Here, a substantia nigra sample obtained from the PD patient is shown in the photographs in an upper row of FIG. 1A, whereas a cerebral cortex sample obtained from the DLB patient is shown in the photographs in a lower row of FIG. 1A. A term "merge" refers to composition of two photographs. Since anti-adiponectin antibody and anti-phosphorylated α (alpha)-synuclein antibody are respectively detected by Alexa Fluor 488 labeled anti-rabbit antibody and Alexa Fluor 594 labeled anti-mouse antibody, adiponectin and phosphorylated α (alpha)-synuclein are respectively stained green and red. When both antigens co-localize, co-localized parts are yellow in the merged photographs. As shown in FIG. 1A, there was observed co-localization of adiponectin (APN) and phosphorylated α (alpha)-synuclein (phosphorylated α (alpha)S) in halos of Lewy bodies.

2.2 Quantification of Protein in Each Soluble Fraction

Figure 1B:
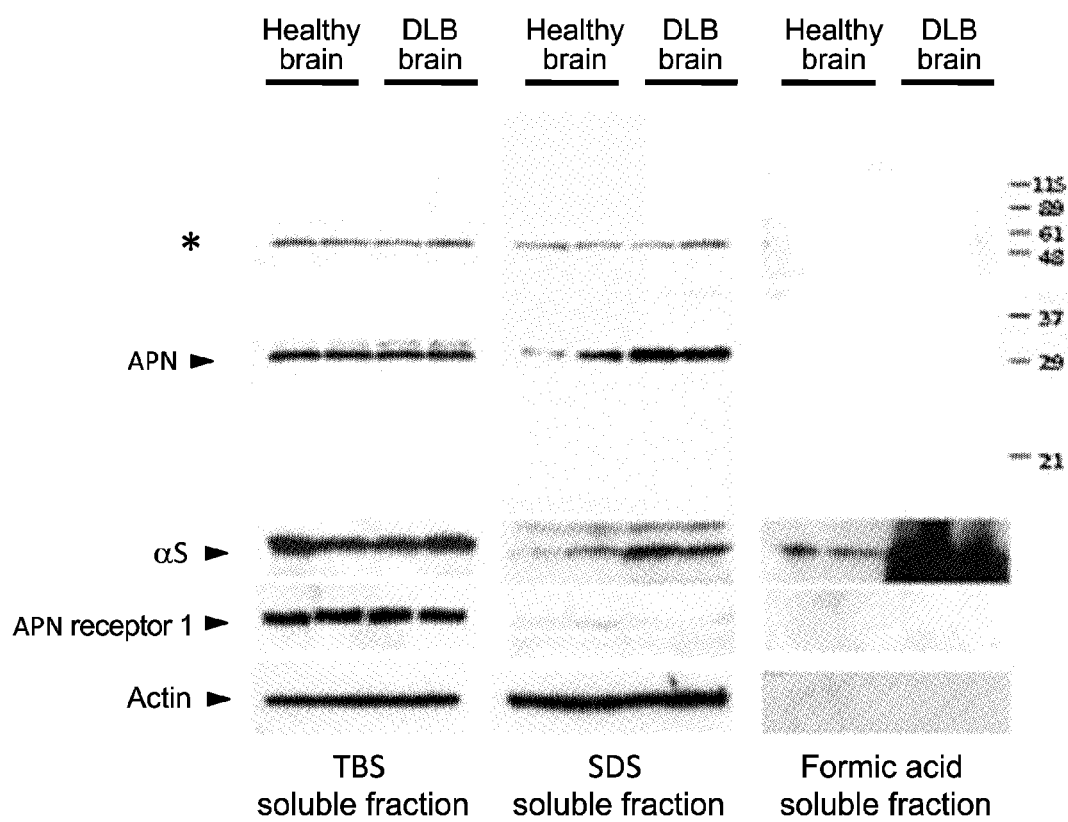
FIG. 1B is a series of western blot images showing results of detecting various extracted fractions using anti-adiponectin antibody, anti-phosphorylated α (alpha)-synuclein antibody, anti-adiponectin receptor 1 antibody and anti-β (beta)-actin antibody, the various extracted fractions being prepared using brain samples of a healthy subject and a DLB patient.
Figure 1C:
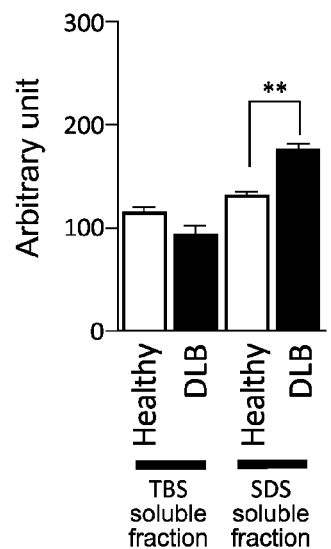
FIG. 1C is a graph summarizing the experimental results of FIG. 1B.

FIG. 1B is a series of western blot images showing results of detecting various extracted fractions using anti-adiponectin antibody, anti-phosphorylated α (alpha)-synuclein antibody, anti-adiponectin receptor 1 antibody and anti-β (beta)-actin antibody, the various extracted fractions being prepared using the brain samples of the healthy subject and the DLB patient. FIG. 1C is a graph summarizing the experimental results of FIG. 1B. Each error bar under each experimental condition represents a standard error in measured values from experimental results obtained after repeating the experiment four times under a same condition. With regard to statistical test, there were employed one-way ANOVA and Tukey's post hoc test (Prism4, GraphPad Software, Inc.). Asterisks (**) indicate that p value was less than 1%. As shown in FIG. 1B and FIG. 1C, APN and phosphorylated α (alpha)-synuclein in the SDS soluble fraction were observed more in the DLB patient than in the healthy subject. Statistically, an amount of adiponectin in the SDS fraction was observed significantly more in the DLB patient than in the healthy subject. Phosphorylated α (alpha)-synuclein in the formic acid soluble fraction was observed more in the DLB patient than in the healthy subject. However, adiponectin was not detected in the formic acid soluble fraction. Accordingly, it was indicated that adiponectin bound to α (alpha)-synuclein aggregates that were soluble in SDS.

Based on conventional knowledge, it has been believed that adiponectin expression does not occur in the adult brain. However, according to the experimental results of this example, there was observed co-localization of adiponectin and phosphorylated α (alpha)-synuclein in halos of Lewy bodies. Further, it was indicated that adiponectin had been insolubilized in the DLB patient. Accordingly, there was shown a possibility that adiponectin and phosphorylated α (alpha)-synuclein participate in the formation of Lewy bodies.

Experimental Example 2

Adiponectin Expression in Thy-1-α (Alpha)S Transgenic Mouse Brain-Specifically Expressing α (Alpha)-Synuclein 1. Material and Method 1.1 Transgenic Animal Thy-1-α (alpha)S transgenic mice neuron-specifically express human α (alpha)-synuclein gene by a Thy-1 promoter (referred to as an α (alpha)S tg mice hereunder: University of California, San Diego, donated by Prof. Eliezer Masliah, Rockenstein et al., J. Neurosci. Res. 66:573(2002)). The α (alpha)S tg mice were reared and bred in an SPF animal room in Tokyo Metropolitan Institute of Medical Science. The α (alpha)S tg mice were crossbred with C57BL/6 (CLEA Japan, Inc.). Here, genetic screening was performed using PCR method. While mice having transgene were categorized as an experimental group, wild-type littermate mice (referred to as non tg mice hereunder) were categorized as a control group. Male α (alpha)S tg mice and non tg mice aged seven months were anesthetized, and then had blood thereof removed by perfusion with 0.1 M phosphate buffered saline (PBS), followed by being euthanized by cervical dislocation. Brain samples were frozen by liquid nitrogen and stored at −80° C.

1.2 Quantification of Adiponectin mRNA

RT-PCR was performed in accordance with a method of Fujita et al. (Fujita et al., Nat. Commun. 1:110 (2010)). Total RNA was extracted from the frozen brain samples of the α (alpha)S tg mice and the non tg mice by ISOGEN (NIPPON GENE CO., LTD.), followed by performing DNase (DNase 1, Invitrogen, Life Technologies Japan Ltd.) treatment at 37° C. for 30 min. Here, cDNA was synthesized from the total RNA of 2.5 μg, using Superscript III First-Strand Synthesis system (Invitrogen, Life Technologies Japan Ltd.).

A reverse transcription product was amplified by PCR using the following primers.

```
Mouse adiponectin forward primer:
                                               (SEQ. No. 1)
5'-CTACAACTGAAGAGCTAGCTCCTG-3'

Mouse adiponectin reverse primer:
                                               (SEQ. No. 2)
5'-CACACTGAACGCTGAGCGATACAC-3'

Rat adiponectin forward primer:
                                               (SEQ. No. 3)
5'-GGACAACAATGGACTCTATGCAGATA-3'

Rat adiponectin reverse primer:
                                               (SEQ. No. 4)
5'-CTACGGGCTGCTCTGAATTAGGTG-3'

Mouse adiponectin receptor 1 (AdipoR1) forward primer:
                                               (SEQ. No. 5)
5'-CAACATCTGGACACATCTGCTTGG-3'

Mouse adiponectin receptor 1 (AdipoR1) reverse primer:
                                               (SEQ. No. 6)
5'-GTAGAGCAATCCCTGAATAGTCCAG-3'

Rat adiponectin receptor 1 (AdipoR1) forward primer:
                                               (SEQ. No. 7)
5'-ATCTTCCGCATCCACACAGAA-3'

Rat adiponectin receptor 1 (AdipoR1) reverse primer:
                                               (SEQ. No. 8)
5'-ATATTTGGTCTGAGCATGGTCAAG-3'

Mouse adiponectin receptor 2 (AdipoR2) forward primer:
                                               (SEQ. No. 9)
5'-TTGGACACATCTCCTAGGTTGTGTA-3'

Mouse adiponectin receptor 2 (AdipoR2) reverse primer:
                                               (SEQ. No. 10)
5'-CACAGATGACAATCAGGTAGATGAAG-3'

Rat adiponectin receptor 2 (AdipoR2) forward primer:
                                               (SEQ. No. 11)
5'-AGATAGGCTGGCTAATGCTCATG-3'

Rat adiponectin receptor 2 (AdipoR2) reverse primer:
                                               (SEQ. No. 12)
5'-GATGTCACATTTGCCAGGAAAG-3'

Mouse and Rat cyclophilin A forward primer:
                                               (SEQ. No. 13)
5'-TCCATGGCAAATGCTGGAC-3'

Mouse and Rat cyclophilin A reverse primer:
                                               (SEQ. No. 14)
5'-GTCTTGCCATTCCTGGACCC-3'
```

A reaction condition of PCR was as follows. That is, PCR was at first performed at 94° C. for 5 min, followed by repeating 35 times a cycle of: 95° C. for 30 sec; 55° C. for 30 sec; and 72° C. for 60 sec. Subsequently, PCR was further performed at 72° C. for 10 min before reaching a stationary state and being left standing at 4° C. PCR products were electrophoresed in 1.2% agarose gel. With regard to an mRNA amount of each gene, concentrations of ethidium bromide-stained bands of the PCR products were quantitated by densitometer (ATTO). mRNA amounts of adiponectin were standardized by mRNA amounts of cyclophilin A.

1.3 Quantification of Protein in Each Soluble Fraction

Extractions of various soluble fractions and detection by western blotting were performed in accordance with the procedures described in example 1. Protein samples were prepared from cerebral cortexes of the α (alpha)S tg mice and the non tg mice by a standard method well known to those skilled in the art. An anti-adiponectin antibody, an anti-adiponectin receptor 1 antibody and an anti-β (beta)-actin antibody were used as primary antibodies. An HRP labeled anti-rabbit IgG antibody, an HRP labeled anti-goat IgG antibody and an HRP labeled anti-mouse IgG antibody (DAKO) were used as secondary antibodies. With regard to an amount of each protein, densities of bands detected by a luminous reaction were quantitated by Image J (NIH: National Institutes of Health). Protein amounts of adiponectin were standardized by protein amounts of β (beta)-actin.

2. Result 2.1 Quantification of Adiponectin mRNA

Figure 2A:
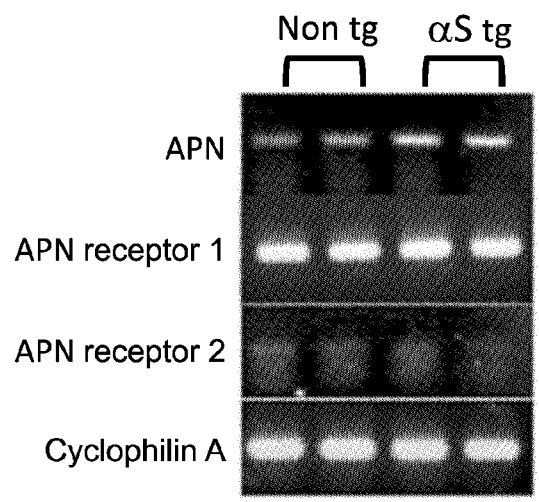
FIG. 2A is an electropherogram of an experiment examining mRNA amounts of adiponectin in α (alpha)S tg mice and non tg mice.
Figure 2B:
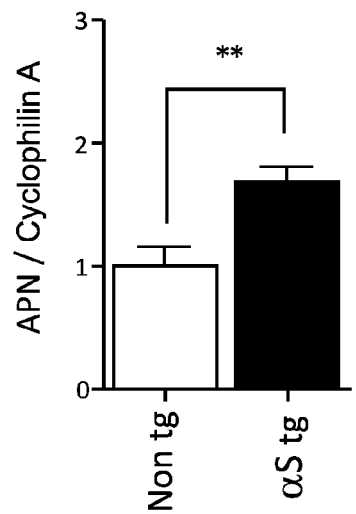
FIG. 2B is a graph summarizing the mRNA amounts observed in the experiment of FIG. 2A.

FIG. 2A is an electropherogram of an experiment examining the mRNA amounts of adiponectin in the brains of the α (alpha)S tg mice and the non tg mice. FIG. 2B is a graph summarizing the mRNA amounts observed in the experiment of FIG. 2A. Each error bar represents a standard error in the mRNA amounts of adiponectin of the α (alpha)S tg mice and the non tg mice (eight to nine for each type of mouse), the mRNA amounts of adiponectin being standardized by cyclophilin A. Asterisks (**) represent that p value was less than 1% in one-way ANOVA and Tukey's post hoc test. Statistically, the mRNA amounts of adiponectin were observed significantly more in the α (alpha)S tg mice than in the non tg mice.

2.2 Quantification of Protein in Each Soluble Fraction

Figure 2C:
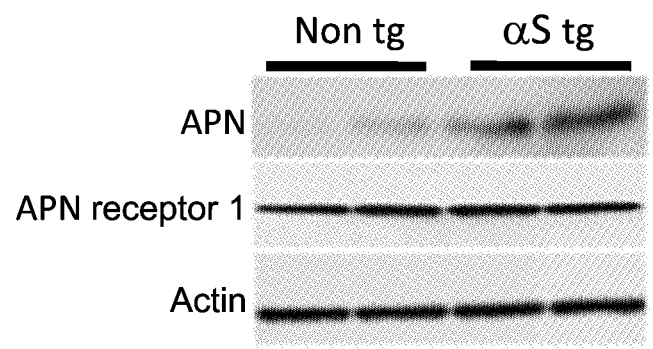
FIG. 2C is a western blot image showing experimental results of protein amounts of adiponectin in the α (alpha)S tg mice and the non tg mice.
Figure 2D:
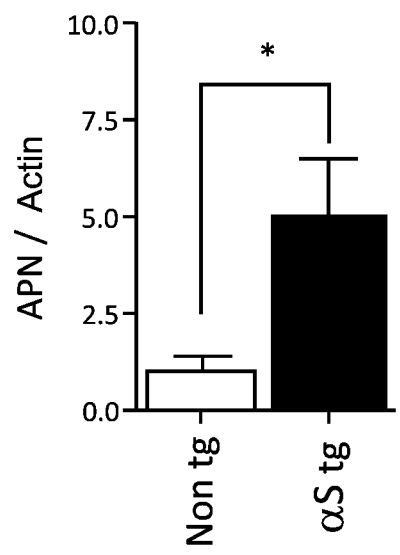
FIG. 2D is a graph summarizing the experimental results of FIG. 2C.

FIG. 2C is a western blot image showing experimental results of the protein amounts of adiponectin in the α (alpha)S tg mice and the non tg mice. FIG. 2D is a graph summarizing the experimental results of FIG. 2C. Each error bar represents a standard error in the protein amounts of adiponectin of the α (alpha)S tg mice and the non tg mice (eight to nine for each type of mouse), the protein amounts of adiponectin being standardized by those of β (beta)-actin. Asterisks (**) represent that p value was less than 5% in one-way ANOVA and Tukey's post hoc test. Statistically, the protein amounts of adiponectin were observed significantly more in the α (alpha)S tg mice than in the non tg mice. As an experimental result of this example, it was indicated that gene expression of adiponectin was induced in the brain expressing α (alpha)-synuclein.

Experimental Example 3

Adiponectin Expression in Cultured Neuron Expressing α (Alpha)-Synuclein

1. Material and Method
  1.1 Cell Culture

Under a condition of 5% $CO_2$ and 37° C., rat B103 neuroblastoma cells were cultured and then subcultured in a high-glucose Dulbecco's modified Eagle's medium (referred to as "DMEM" hereunder. GIBCO, Invitrogen, Life Technologies Japan Ltd.), the DMEM containing 10% fetal bovine serum (FBS, BioWest, Funakoshi Co., Ltd.) and 1% v/v penicillin/streptomycin (catalog number: 15070-063, Invitrogen, Life Technologies Japan Ltd.).

1.2 Preparation of B103 Rat Neuroblastoma Cells Artificially Expressing α (Alpha)-Synuclein A construct of pCEP4-α (alpha)-synuclein prepared by Takenouchi et al. (Takenouchi et al., Mol. Cell. Neurosci., 17:141(2001)) was used to constantly express α (alpha)-synuclein cDNA. B103 neuroblastoma cells transfected with the construct of pCEP4-α (alpha)-synuclein (referred to hereunder as B103 neuroblastoma cells (α (alpha)S) were prepared in accordance with procedures described by Takenouchi et al. (Mol. Cell. Neurosci., 17:141(2001)). As a control group, there were used B103 neuroblastoma cells transfected with an empty pCEP4 expression vector without α (alpha)-synuclein cDNA (referred to hereunder as B103 neuroblastoma cells (vector)). The B103 cells transfected with the aforementioned construct were selected in the presence of hygromycin (100_m/mL, Calbiochem, Merck & Co., Inc.), thereby obtaining hygromycin-resistant B103 cell clones among which clones stably-expressing α (alpha)-synuclein were used as neuroblastoma cells expressing α (alpha)-synuclein in an experiment of this example.

1.3 Quantifications of Adiponectin mRNA and Protein

Quantifications of adiponectin mRNA and protein in the B103 neuroblastoma cells (α (alpha)S) and the B103 neuroblastoma cells (vector), were performed in accordance with the procedures described in example 1 and example 2.

1.4 Immunohistochemical Staining

Each cell was proliferated on a polylysine-coated cover glass, fixed with 4% paraformaldehyde for 15 min in a state of about 70% confluence, and further treated with 0.1% TritonX-100 (Sigma-Aldrich Japan Inc.) for 15 min, thus enhancing permeability of cell membrane. Each cell was washed with PBS and then fixed for 30 min with 10% goat normal serum (Vector, Funakoshi Co., Ltd.)/0.1% BSA/TBS. After being washed with PBS, each cell was incubated overnight at 4° C. with the primary antibodies diluted with 0.1% BSA/TBS. After washing, each cell was further incubated for an hour at room temperature with Alexa Fluor labeled secondary antibodies diluted with 0.1% BSA/TBS. After embedding, each cell was observed using a confocal laser scanning microscope (FV1000, Olympus Corporation).

2. Result 2.1 Quantification of Adiponectin mRNA

Figure 3A:
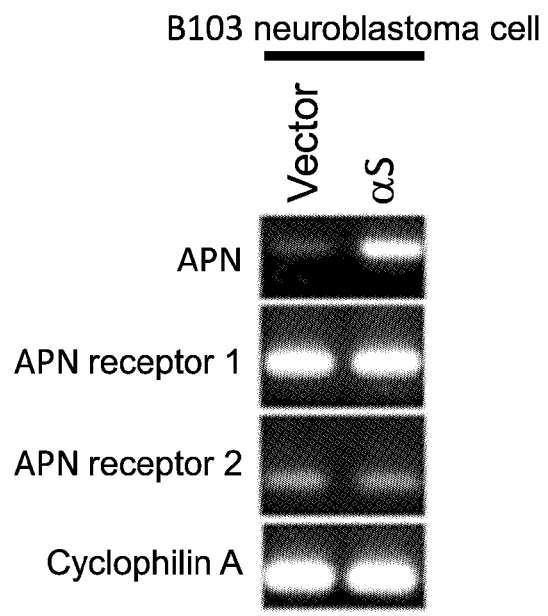
FIG. 3A is an electropherogram obtained from an experiment examining mRNA amounts of adiponectin in B103 neuroblastoma cells (α (alpha)S) and B103 neuroblastoma cells (vector).
Figure 3B:
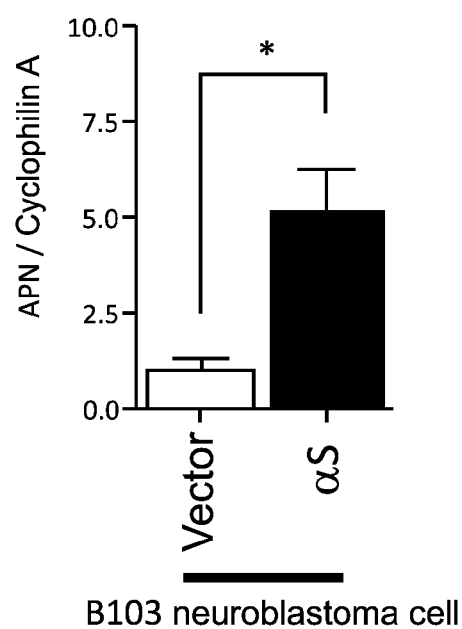
FIG. 3B is a graph summarizing the mRNA amounts of FIG. 3A.

FIG. 3A is an electropherogram obtained from the experiment examining the mRNA amounts of adiponectin in the B103 neuroblastoma cells (α (alpha)S) and the B103 neuroblastoma cells (vector). FIG. 3B is a graph summarizing the mRNA amounts of FIG. 3A. Each error bar represents a standard error in the protein amounts of adiponectin that were standardized by cyclophilin A of six samples of a same condition. An asterisk (*) represents that p value was less than 5% in one-way ANOVA and Tukey's post hoc test. Statistically, the mRNA amounts of adiponectin, as shown in FIG. 3A and FIG. 3B, were observed significantly more in the neuroblastoma cells that were transfected with the construct of pCEP4-α (alpha)-synuclein and expressed α (alpha)-synuclein, than in the control group in which the neuroblastoma cells were transfected with the empty vector.

2.2 Quantification of Protein in Each Soluble Fraction

Figures 3C, 3D:
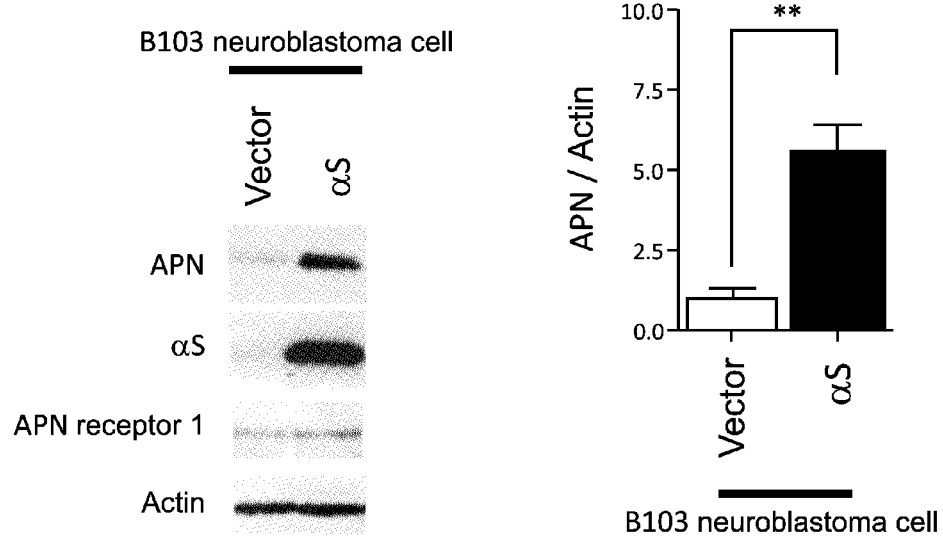
FIG. 3C is a western blot image obtained after detecting surfactant soluble fractions in the B103 neuroblastoma cells (α (alpha)S), using anti-adiponectin antibody, anti-α (alpha)-synuclein antibody, anti-adiponectin receptor 1 antibody and anti-β (beta)-actin antibody.
FIG. 3D is a graph summarizing quantitative results of adiponectin protein in FIG. 3C.

FIG. 3C is a western blot image obtained after detecting surfactant soluble fractions of the B103 neuroblastoma cells (α (alpha)S), using anti-adiponectin antibody, anti-α (alpha)-synuclein antibody, anti-adiponectin receptor 1 antibody and anti-β (beta)-actin antibody. FIG. 3D is a graph summarizing the quantitative results of adiponectin protein in FIG. 3C. Each error bar represents a standard error in the protein amounts of adiponectin that were standardized by β (beta)-actin of six samples of a same condition. Asterisks (**) represent that p value was less than 1% in one-way ANOVA and Tukey's post hoc test. Statistically, the protein amounts of adiponectin were observed significantly more in the B103 neuroblastoma cells (α (alpha)S) that were transfected with the construct of pCEP4-α (alpha)-synuclein and expressed α (alpha)-synuclein, than in the control group in which the B103 neuroblastoma cells were transfected with the empty vector.

2.3 Immunohistochemical Staining

Figure 3E:
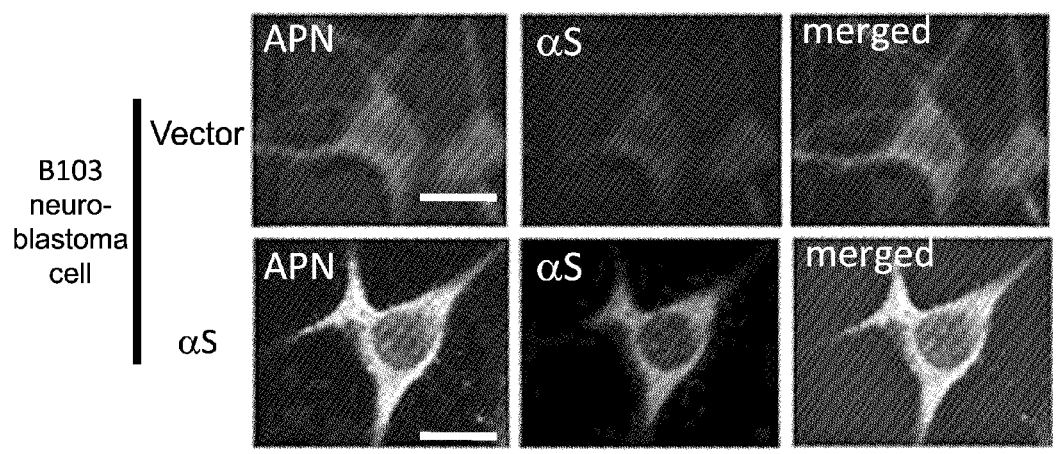
FIG. 3E is a series of confocal microscopic photographs of the B103 neuroblastoma cells (α (alpha)S) and the B103 neuroblastoma cells (vector).

FIG. 3E is a series of confocal microscopic photographs of the B103 neuroblastoma cells (α (alpha)S) and the B103 neuroblastoma cells (vector). The kind of the primary antibody used is shown in the upper left section of each photograph in FIG. 3E. Here, while the B103 neuroblastoma cells (α (alpha)S) are shown in an upper row of FIG. 3E, the B103 neuroblastoma cells (vector) are shown in a lower row of FIG. 3E. Further, A term "merge" refers to composition of two photographs. Since anti-adiponectin antibody and anti-α (alpha)-synuclein antibody are respectively detected by Alexa Fluor 488 labeled anti rabbit antibody and Alexa Fluor 594 labeled anti mouse antibody, adiponectin and α (alpha)-synuclein are respectively stained green and red. Particularly, when both antigens co-localize, co-localized parts are yellow in the merged photographs. As shown in FIG. 3E, there was observed co-localization of adiponectin (APN) and α (alpha)-synuclein (α (alpha)S) in perinuclear area of B103 neuroblastoma cells. According to an experimental result of this example, it was indicated that adiponectin had been expressed and co-localized with α (alpha)-synuclein in the B103 neuroblastoma cells (α (alpha)S). Accordingly, it was indicated that an expression of adiponectin was induced by an expression of α (alpha)-synuclein.

Experimental Example 4

Suppression of Adiponectin Expression Using siRNA

1. Material and Method 1.1 siRNA Transduction

Rat adiponectin sense strand RNA: 5'-CAAUGACUCUA-CAUUUACAtt-3' (SEQ. No. 15), antisense strand RNA: 5'-UGUAAAUGUAGAGUCAUUGtt-3' (SEQ. No. 16), sense strand RNA of random sequence in control experiment: 5'-UCUUAAUCGCGUAUAAGGCtt-3' (SEQ. No. 17) and antisense strand RNA: 5'-GCCUUAUACGCGAUUAA-GAtt-3' (SEQ. No. 18) were prepared utilizing Takara siRNA Design Support System (http://www.takara-bio.co.jp/rnai/) (Takara Bio Inc.). The B103 neuroblastoma cells (α (alpha)S) and the B103 neuroblastoma cells (vector) for the control experiment were cultured using a commercially available 6-well plate, and were transfected using Lipofectamine 2000 (Invitrogen, Life Technologies Japan Ltd.) in a state of 30-50% confluence. After performing transfection for six hours, a medium was replaced with a DMEM containing 10% FBS. After performing cultivation for 24 hours, the medium was then replaced with a serum-free DMEM medium so as to avoid effects of adiponectin. After performing cultivation for another three days, transfected B103 neuroblastoma cells were collected so as to be subjected to a detection of an aggregate state of α (alpha)-synuclein and a measurement of proteasomal activity. Further, transfection to B103 neuroblastoma cells for thioflavin T staining were carried out on a polylysine-coated cover glass. After cultivating the aforementioned B103 neuroblastoma cells in a serum-free medium, the cells were then fixed with 4% paraformaldehyde for 20 min. After washing the aforementioned B103 neuroblastoma cells with PBS, the cells were then stained for 7 min with 0.1% thioflavin T (Sigma-Aldrich Japan Inc.).

1.2 Extraction of Each Soluble Fraction and Detection by Western Blotting

Extraction of each soluble fraction and quantification of protein in each soluble fraction by western blotting were performed in accordance with procedures similar to those of example 1 through example 3.

1.3 Measurement of Proteasomal Activity siRNA-transduced B103 neuroblastoma cells were collected with HEPES buffer (50 mM HEPES (pH 7.4), 10 mM EDTA, 10 mM NaCl). Next, cell membranes were disrupted by repeating freezing and thawing, and a supernatant was then collected by performing centrifugation at 20,000×g, 4° C. for 10 min. Protein concentrations were measured, and 10 tg thereof was dissolved in HEPES buffer containing 40 μM of benzyloxycarbonyl-Leu-Leu-Glu-amidomethylcoumarin fluorescent proteasome substrate (Chemicon, Japan Millipore Corporation). Proteasomal activity was calculated as follows. That is, a disintegrated amount of substrate was measured by Berthold Mithras LB940 microplate reader (Berthold Japan co. ltd.), according to time for one hour and at 37° C. (excitation wavelength 380 nm, measurement wavelength 460 nm).

2. Result

Figure 4A:
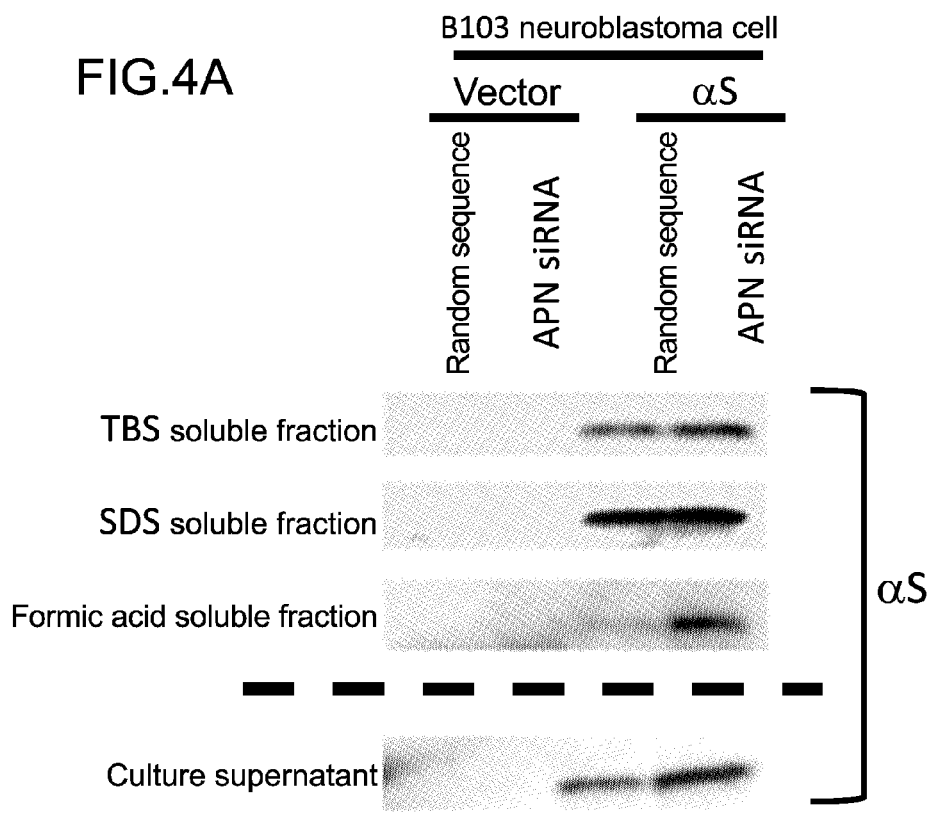
FIG. 4A is a western blot image showing results of an experiment examining an effect of adiponectin siRNA on an aggregate state of α (alpha)-synuclein protein in the B103 neuroblastoma cells (α (alpha)S) and the B103 neuroblastoma cells (vector).

FIG. 4A is a western blot image showing results of an experiment examining an effect of adiponectin siRNA on an aggregate state of α (alpha)-synuclein protein in the B103 neuroblastoma cells (α (alpha)S) and the B103 neuroblastoma cells (vector). Specifically, the results of the experiment were obtained as follows. That is, either adiponectin antisense strand siRNA (APN siRNA) or siRNA of random sequence used in the control experiment (random sequence) was transduced to the B103 neuroblastoma cells (α (alpha)S) and the B103 neuroblastoma cells (vector) for the control experiment. The cells were then cultivated for 72 hours, followed by obtaining each soluble fraction by successive extraction using TBS, SDS and then formic acid, thus allowing supernatants and the aforementioned soluble fractions to be analyzed by western blotting. As shown in FIG. 4A, when the expression of adiponectin in the B103 neuroblastoma cells (α (alpha)S) was not suppressed by siRNA, although α (alpha)-synuclein was detected in supernatants, TBS and SDS soluble fractions, it was not detected in the formic acid soluble fraction. However, when the expression of adiponectin was suppressed by siRNA, α (alpha)-synuclein was also detected in the formic acid soluble fraction.

Figure 4B:
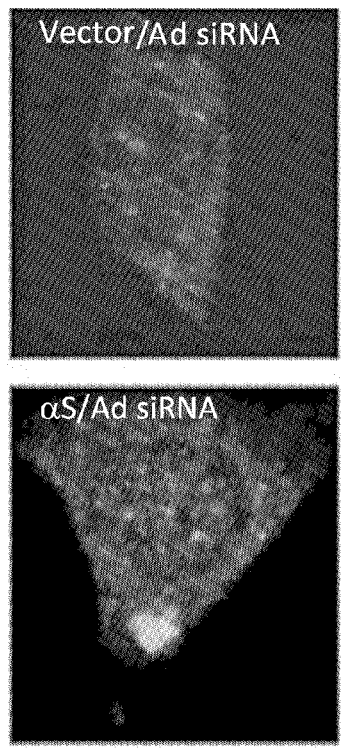
FIG. 4B is a set of confocal microscopic photographs of thioflavin T stained cells, the confocal microscopic photographs showing the results of the experiment studying the effect of adiponectin siRNA on the aggregate state of α (alpha)-synuclein protein in the B103 neuroblastoma cells (α (alpha)S/Ad siRNA) and the B103 neuroblastoma cells (vector/Ad siRNA).

FIG. 4B is a set of confocal microscopic photographs of thioflavin T stained cells, the confocal microscopic photographs showing the results of the experiment studying the effect of adiponectin siRNA on the aggregate state of α (alpha)-synuclein protein in the B103 neuroblastoma cells (α (alpha)S/Ad siRNA) and the B103 neuroblastoma cells (vector/Ad siRNA). In order to confirm aggregation of protein, thioflavin T staining was performed on both: the adiponectin antisense strand siRNA-transduced B103 neuroblastoma cells expressing α (alpha)-synuclein (α (alpha)S/Ad siRNA); and the B103 neuroblastoma cells for the control experiment that are transfected with the empty expression vector (vector/Ad siRNA). As a result, thioflavin T-positive image was observed in the α (alpha)-synuclein expressing neuroblastoma cells in which expression of adiponectin was suppressed, thus indicating aggregation of protein.

Figure 4C:
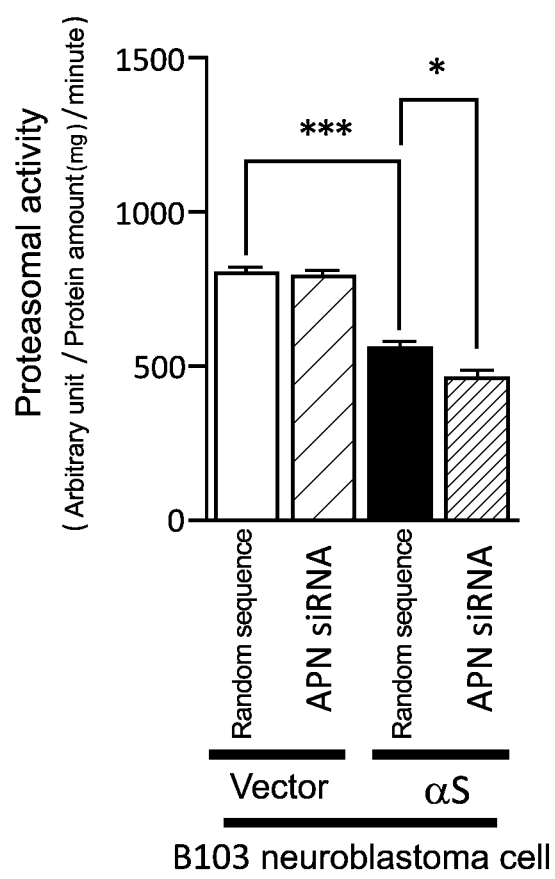
FIG. 4C is a graph summarizing the experimental results in FIG. 4A.

FIG. 4C is a graph summarizing the experimental results in FIG. 4A. Each error bar represents a standard error in measured values of proteasomal activity of 4 to 5 samples of a same condition. An asterisk (*) represents that p value was less than 5% in one-way ANOVA and Tukey's post hoc test. Asterisks (***) represent that p value was less than 0.1% in one-way ANOVA and Tukey's post hoc test. As shown in FIG. 4C, proteasomal activity was low in the B103 neuroblastoma cells (α (alpha)S/Ad siRNA), as compared to the B103 neuroblastoma cells (vector/Ad siRNA) for the control experiment. In addition, proteasomal activity was low in the B103 neuroblastoma cells to which siRNA of adiponectin had been transduced, as compared to the B103 neuroblastoma cells to which siRNA of random sequence had been transduced. According to the experimental result of this example, it was indicated that expression of α (alpha)-synuclein reduced proteasomal activity, and that adiponectin partially inhibited a decrease in proteasomal activity.

Experimental Example 5

Induction of Adiponectin Expression by Inhibiting Proteasomal Function

1. Material and Method

MG132 (Calbiochem, Merck & Co., Inc.) was used as a proteasome inhibitor. Particularly, there were prepared: a stock solution by dissolving 10 mM MG132 in DMSO; and a 10% FBS-added DMEM medium containing 10_μM MG132 just before use. A medium of the B103 neuroblastoma cells in a state of 80-90% confluence was replaced with the 10% FBS-added DMEM medium containing MG132. Six hours later, the aforementioned cells were collected, and expression of adiponectin mRNA was measured by RT-PCR.

2. Result

Figure 5A:
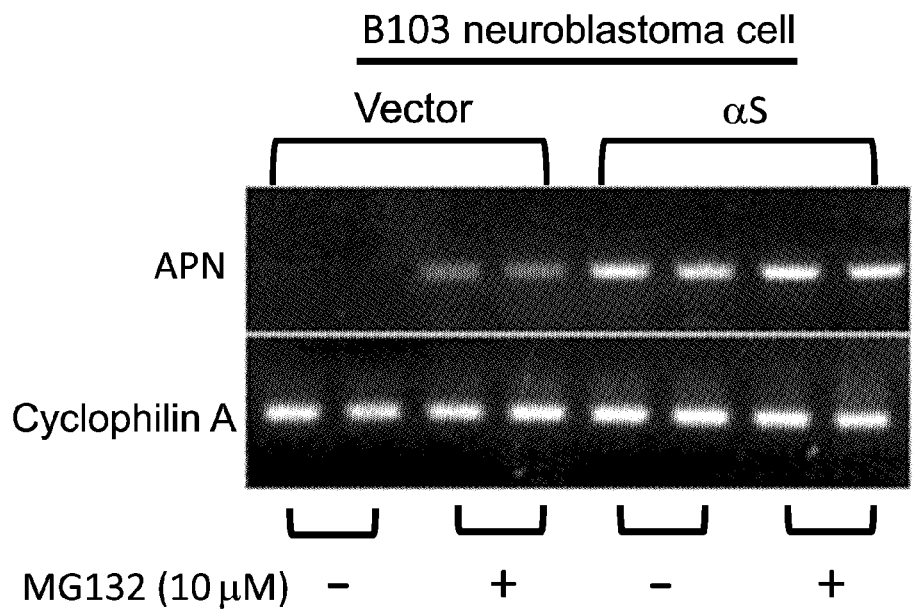
FIG. 5A is an electropherogram of an experiment examining an effect on the mRNA amounts of adiponectin when 10 μM MG132 was (+) or was not (−) added to the B103 neuroblastoma cells (α (alpha)S) and the B103 neuroblastoma cells (vector).
Figure 5B:
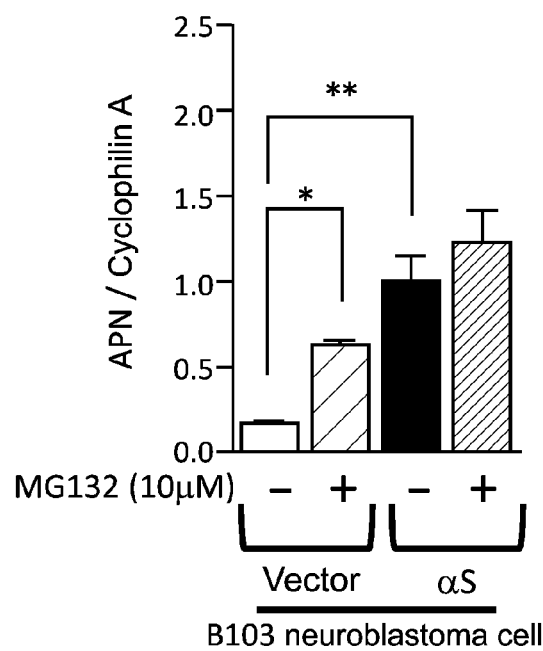
FIG. 5B is a graph summarizing the experimental results of FIG. 5A.

FIG. 5A is an electropherogram of an experiment examining an effect on the mRNA amounts of adiponectin when 10 μM MG132 was (+) or was not (−) added to the B103 neuroblastoma cells (α (alpha)S) and the B103 neuroblastoma cells (vector). FIG. 5B is a graph summarizing the experimental results of FIG. 5A. Each error bar represents a standard error in the mRNA amounts of adiponectin that were standardized by cyclophilin A of 5 to 6 samples of a same condition. An asterisk (*) represents that p value was less than 5% in one-way ANOVA and Tukey's post hoc test. Asterisks (**) represent that p value was less than 1% in one-way ANOVA and Tukey's post hoc test. As shown in FIG. 5B, expression of adiponectin was induced in the B103 neuroblastoma cells artificially expressing α (alpha)-synuclein. However, regardless of the presence of α (alpha)-synuclein expression, induction of adiponectin expression increased as proteasomal activity was decreased by MG132.

Experimental Example 6

Effect on α (Alpha)-Synuclein Aggregation and Proteasomal Activity Due to Overexpression of Adiponectin 1. Material and Method 1.1 Preparation of Adiponectin Expression Vector Construct A primer containing specific sequence to adiponectin was designed using gene library of mouse cDNA. There were prepared: a forward primer containing adiponectin N-terminal sequence (N-adiponectin) 5'-GGGATGCTACTGTTG-CAAGCT-3' (SEQ. No. 19); and a reverse primer containing adiponectin C-terminal sequence (C-adiponectin) 5'-GAG-TAGTTGCAGTCAGTTGGTATCATG-3' (SEQ. No. 20). Here, mouse adiponectin cDNA was amplified by PCR reaction, using a cDNA template obtained from mouse adipose tissue. DNA fragment obtained was separated with 1% agarose gel, and band of adiponectin cDNA was cut out from the gel, thus purifying DNA. Later, phosphate group was attached to 5' terminus of the adiponectin cDNA fragment by T4 polynucleotide kinase (Takara Bio Inc.). pCEP4 vector (Invitrogen, Life Technologies Japan Ltd.) previously digested by restriction enzyme PvuII was dephosphorylated with alkaline phosphatase. Phosphorylated adiponectin fragment was inserted into PvuII site of dephosphorylated pCEP4 by T4 ligase (Takara Bio Inc.). As a result, there was obtained pCEP4-APN expression vector construct containing full length sequence of adiponectin. Later, construction of pCEP4-APN was confirmed by determining the nucleic acid sequence thereof.

1.2 Preparation of Adiponectin-Overexpressing B103 Neuroblastoma Cells (α (Alpha)S)

Adiponectin stably-expressing B103 rat neuroblastoma cells were prepared by transfecting the pCEP4-APN expression vector construct to the B103 rat neuroblastoma cells (α (alpha)S) and the B103 rat neuroblastoma cells (vector). Briefly, pCEP4-APN was transfected to the B103 neuroblastoma cells (α (alpha)S) and the B103 neuroblastoma cells (vector) in a state of about 80% confluence, using Lipofectamine 2000 (Invitrogen, Life Technologies Japan Ltd.). As a control, the empty pCEP4 expression vector was transfected to the B103 neuroblastoma cells (α (alpha)S) and the B103 neuroblastoma cells (vector). After transfection, culture medium was replaced with DMEM medium, and the cells were then collected after 48 hours.

Solubility of α (alpha)-Synuclein

Later, there were prepared the TBS soluble fraction, the SDS soluble fraction and the formic acid soluble fraction in accordance with the procedures described in example 1. Expression of adiponectin and solubility of α (alpha)-synuclein were confirmed by western blotting. Here, western blotting was performed in accordance with the procedures described in example 1.

Measurement of Proteasomal Activity 0, 0.5 or 1_m/well of pCEP4-APN was transfected to the B103 cells (α (alpha)S) cultured in the 6-well plate (closed column). As a control, the empty pCEP4 expression vector was transfected to the B103 cells (vector) cultured (open column). The cells thus transfected were collected with HEPES buffer after 48 hours, and then subjected to measurement of proteasomal activity. Here, measurement of proteasomal activity was performed in accordance with the procedures described in example 4.

2. Result

Figure 6A:
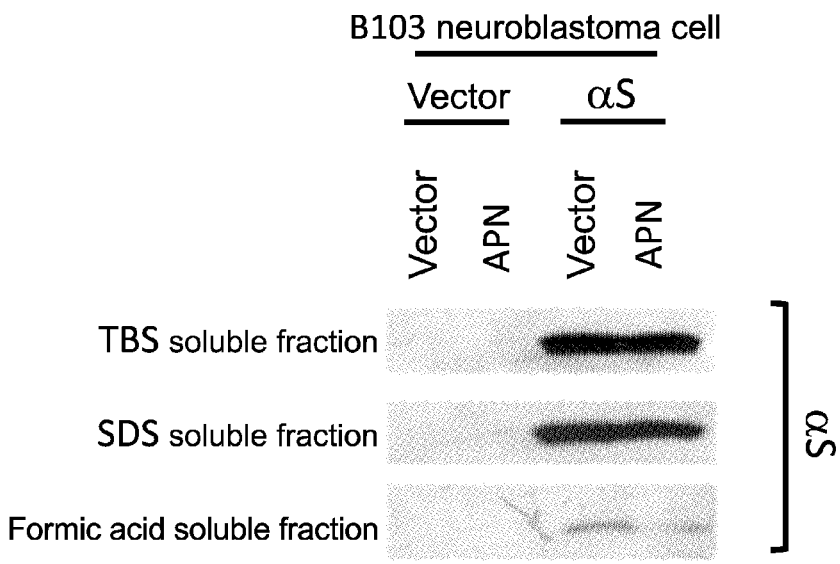
FIG. 6A is a western blot image showing results of an experiment examining an effect of transient expression of adiponectin in the B103 neuroblastoma cells (α (alpha)S) and the B103 neuroblastoma cells (vector).

FIG. 6A is a western blot image showing results of an experiment examining an effect of transient expression of adiponectin in the B103 neuroblastoma cells (α (alpha)S) and the B103 neuroblastoma cells (vector). As shown in FIG. 6A, α (alpha)-synuclein was detected in all the TBS soluble fraction, the SDS soluble fraction and the formic acid soluble fraction, when transient expression of adiponectin was not performed in the B103 neuroblastoma cells (α (alpha)S). However, when transient expression of adiponectin was performed in the B103 neuroblastoma cells (α (alpha)S), α (alpha)-synuclein was detected in the TBS soluble fraction and the SDS soluble fraction, but not in the formic acid soluble fraction. This indicated that insoluble aggregates of α (alpha)-synuclein had not been formed in SDS, when adiponectin was overexpressed. That is, aggregation of α (alpha)-synuclein was suppressed by overexpression of adiponectin.

Figure 6B:
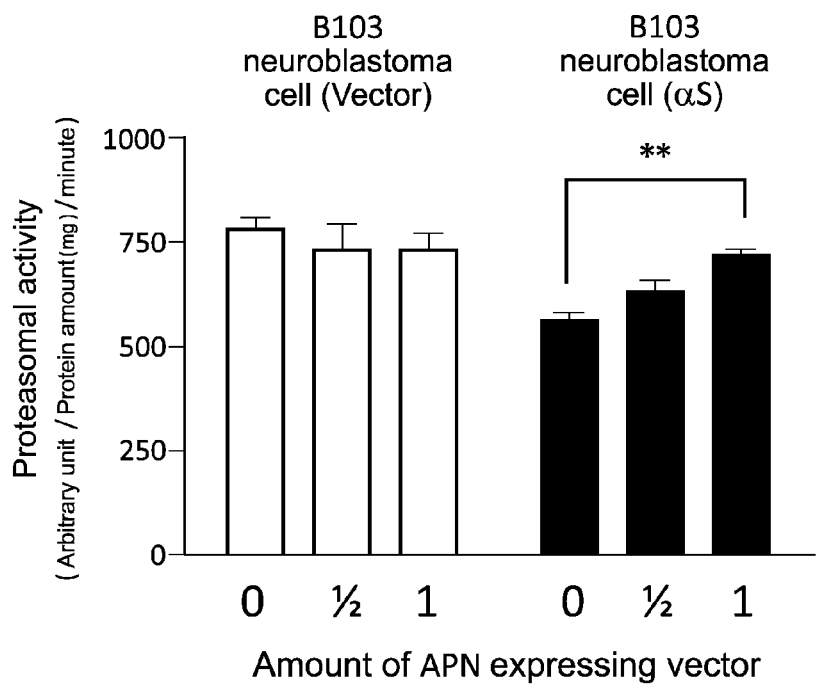
FIG. 6B is a graph showing results of an experiment examining an effect of transient expression of adiponectin on proteasomal activity in the B103 neuroblastoma cells (α (alpha) S) and the B103 neuroblastoma cells (vector), the effect being caused by α (alpha)-synuclein protein.

FIG. 6B is a graph showing results of an experiment examining an effect of transient expression of adiponectin on proteasomal activity in the B103 neuroblastoma cells (α (alpha) S) and the B103 neuroblastoma cells (vector), the effect being caused by α (alpha)-synuclein protein. Each error bar represents a standard error in measured values of proteasomal activity of 5 to 7 samples of a same condition. Asterisks (**) represent that p value was less than 1% in one-way ANOVA and Tukey's post hoc test. As shown in FIG. 6B, the decrease in proteasomal activity due to α (alpha)-synuclein was substantially recovered in the B103 neuroblastoma cells (α (alpha)S) transiently expressing adiponectin. This indicated that overexpression of adiponectin caused an effect of treating and/or improving neurodegenerative disease caused by α (alpha)-synuclein.

Experimental Example 7

Protein-Protein Interaction of α (Alpha)-Synuclein and Adiponectin

1. Material and Method

Human adiponectin recombinant protein (ProSpec, IWAI CHEMICALS COMPANY LTD.) 0.5 μg and human α (alpha)-synuclein recombinant protein (Hashimoto et al., Brain Res. 799:301 (1998)) 1.0 μg were incubated for 48 hours in 100 mM sodium acetate solution at 37° C., 500 rpm (Thermomixer, Eppendorf Co., Ltd.). Later, an analysis via western blotting was performed in accordance with procedures similar to those in example 1 through example 6. Each sample was dissolved in 1× sample buffer without 2ME, and heated at 95° C. for 10 min. With regard to a control experiment, incubation was performed at room temperature. Particularly, instead of α (alpha)-synuclein, BSA (1.0 μg) was incubated with adiponectin.

2. Result

Figure 7A:
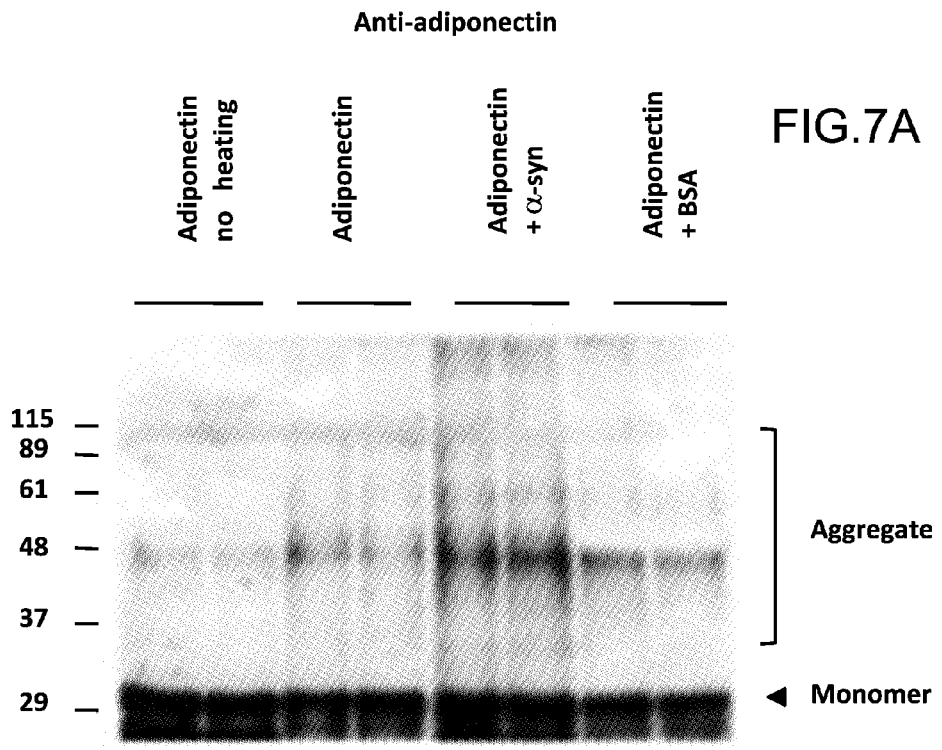
FIG. 7A is a western blot image showing results of an experiment examining: an aggregation of adiponectin recombinant protein in test tube; and an effect of α (alpha)-synuclein recombinant protein on such aggregation.

FIG. 7A is a western blot image showing results of an experiment examining: an aggregation of adiponectin recombinant protein in test tube; and an effect of α (alpha)-synuclein recombinant protein on such aggregation. There were prepared two different samples under each experimental condition, and performed electrophoresis in adjacent lanes. As shown in FIG. 7A, while dimer and trimer of adiponectin were detected at room temperature, the dimer thereof increased through incubation at 37° C. When performing incubation of adiponectin with α (alpha)-synuclein, the dimer of adiponectin further increased, and adiponectin aggregates which are hardly separable were detected on the upper end of the gel. Instead of α (alpha)-synuclein, when performing incubation with adiponectin and BSA, an aggregated state of adiponectin was substantially similar to that observed when performing incubation with adiponectin alone.

Figure 7B:
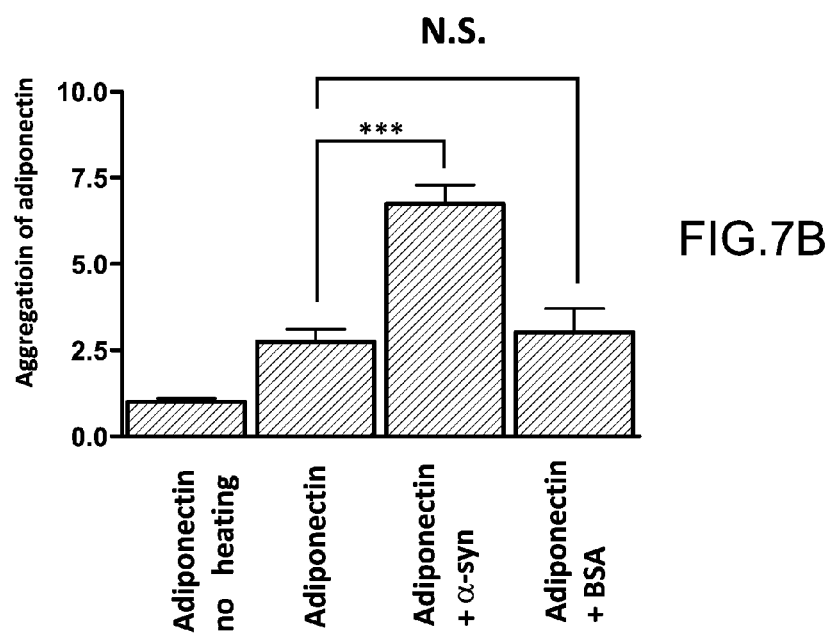
FIG. 7B is a graph summarizing the experimental results in FIG. 7A.

FIG. 7B is a graph summarizing the experimental results in FIG. 7A. Each error bar represents a standard error in densitometer values of a range of 45 samples of a same condition, the range being titled "aggregate" on a left side of the western blot image of FIG. 7A. Asterisks (***) represent that p value was less than 0.5% in one-way ANOVA and Tukey's post hoc test. A symbol "N.S." represents that no significant difference was observed by the test. As evident from FIG. 7B, adiponectin aggregation was significantly promoted in the presence of α (alpha)-synuclein.

The results of this example indicated that there existed a direct protein-protein interaction between adiponectin and α (alpha)-synuclein. Accordingly, it is considered that adiponectin contributes not only to inhibition or suppression of α (alpha)-synuclein aggregation in neuron, but also to suppression or reduction of extracellular formation of α (alpha)-synuclein aggregates.

Experimental Example 8

Effect of Adiponectin on α (Alpha)-Synuclein Aggregation, Signal Transduction and Tau Phosphorylation 1. Material and Method 1.1 Experiment Regarding Adiponectin Addition (1) (α (Alpha)-Synuclein Aggregation)

The B103 neuroblastoma cells (α (alpha)S) and the B103 neuroblastoma cells (vector) were prepared and cultured in accordance with the procedures described in example 3. The B103 neuroblastoma cells (α (alpha)S) and the B103 neuroblastoma cells (vector) were inoculated on the 6-well plate and cultured to a state of about 80-90% confluence. After washing with PBS, the aforementioned cells were further cultured for 24 hours in a test medium prepared by adding recombinant human adiponectin (1 μg/mL, trimer, PROSPEC) to a serum-free medium. As a control, there was used a control medium prepared by adding thereto PBS instead of recombinant human adiponectin. After culturing, there were prepared the TBS soluble fraction, the SDS soluble fraction and the formic acid soluble fraction in accordance with the procedures described in example 1. Further, western blotting was performed in accordance with the procedures described in example 1. In order to evaluate α (alpha)-synuclein aggregation, an anti-α (alpha)-synuclein mouse monoclonal antibody (syn-1, Nippon Becton Dickinson Company, Ltd) was used as a primary antibody when performing western blotting, the anti-α (alpha)-synuclein mouse monoclonal antibody being diluted appropriately before use. Additionally, an HRP labeled anti-mouse IgG antibody (DAKO) was used as a secondary antibody, the HRP labeled anti-mouse IgG antibody being diluted appropriately before use.

1.2 Experiment Regarding Adiponectin Addition (2) (Signal Transduction and Tau Phosphorylation)

The B103 neuroblastoma cells (α (alpha)S) and the B103 neuroblastoma cells (vector) were inoculated on a 5 cm dish and cultured to a state of about 80-90% confluence. Later, the aforementioned cells were washed with PBS, and then cultured in a serum-free medium for four hours. After washing with PBS, the cells were then cultured in a test medium (adiponectin-added group) prepared by adding recombinant human adiponectin (1_μg/mL, trimer, PROSPEC) to a serum-free medium. As a control, there was used a control medium (adiponectin non-added group) prepared by adding thereto PBS instead of recombinant human adiponectin. A culture time was 0, 10 and 30 min when evaluating signal transduction, 0, 1 and 2 hour(s) when evaluating tau phosphorylation. The cells collected were lysed with a cell lysis solution (1% TritonX-100, 1% Nonidet P-40, 50 mM HEPES, 150 mM NaCl, 10% glycerol, 1.5 mM $MgCl_2$, 1 mM EGTA, 100_mM sodium fluoride, a protease inhibitor (NACALAI TESQUE, INC.)). Supernatants were collected after performing centrifugation at 100,000×g for 30 min, and were used as surfactant soluble fractions when performing western blotting. Here, western blotting was performed in accordance with the procedures described in example 1.

In order to evaluate signal transduction, an anti-phospho-AMPKα (alpha) (Thr172) antibody (Cell Signaling Technology), an anti-AMPKα (alpha) antibody (Cell Signaling Technology), an anti-phospho-p38 MAPK (Thr180/Thr182) antibody (D3F9, Cell Signaling Technology), an anti-p38α (alpha)/SAPK2a antibody (BD Biosciences), an anti-phospho-GSK-3β (beta) (Ser9) antibody (D85E12, Cell Signaling Technology), an anti-GSK-3β (beta) antibody (BD Biosciences) and an anti-β (beta)-actin mouse monoclonal antibody (C-15, Sigma-Aldrich Japan Inc.) were used as primary antibodies after being appropriately diluted. Further, the HRP labeled anti-mouse IgG antibody (DAKO) was used as a secondary antibody after being appropriately diluted.

When performing western blotting to evaluate tau phosphorylation, an anti-phosphorylated tau (Ser 202) antibody (ANASPEC), an anti-phosphorylated tau (Ser 396) antibody (ANASPEC) and the anti-β (beta)-actin mouse monoclonal antibody (C-15, Sigma-Aldrich Japan Inc.) were used as primary antibodies after being appropriately diluted. Further, the HRP labeled anti-mouse IgG antibody (DAKO) was used as a secondary antibody after being appropriately diluted.

1.3 Experiment Regarding Addition of p38 MAPK Inhibitor and AMPK Inhibitor

The aforementioned B103 neuroblastoma cells (α (alpha)S) were inoculated on the 6-well plate and cultured to a state of about 80-90% confluence. After washing with PBS, the aforementioned cells were further cultured for 10 min in an inhibition test medium prepared by adding either 5 µM p38 MAPK inhibitor (SB203580, Promega) or 5 µM AMPK inhibitor (Compound C, Calbiochem) to a serum-free medium. As a control, DMSO was added to a serum-free medium instead of the aforementioned inhibitors. Later, either recombinant human adiponectin (1 µg/mL, trimer, PROSPEC) or PBS was added so as to culture the cells for 30 min. The cells collected were then lysed with the aforementioned cell lysis solution. Supernatants were collected after performing centrifugation at 100,000×g for 30 min, and then subjected to western blotting. Here, western blotting was performed in accordance with the procedures described in example 1.

When performing western blotting to evaluate signal transduction pathways, the anti-phospho-GSK-3β (beta) (Ser9) antibody (D85E12, Cell Signaling Technology), the anti-GSK-3β (beta) antibody (BD Biosciences) and the anti-β (beta)-actin mouse monoclonal antibody (C-15, Sigma-Aldrich Japan Inc.) were used as primary antibodies after being appropriately diluted. Further, the HRP labeled anti-mouse IgG antibody (DAKO) was used as a secondary antibody after being appropriately diluted.

1.4 Immunoprecipitation

Immunoprecipitation was performed by standard procedures known to those skilled in the art. Briefly, the B103 neuroblastoma cells (α (alpha)S) were inoculated on a 10 cm dish, and were cultured to a state of about 80-90% confluence. The cells were then washed with PBS, followed by being cultured in a test medium (adiponectin-added group) prepared by adding recombinant human adiponectin (1 µg/mL, trimer, PROSPEC) to a serum-free medium. As a control, there was used a control medium (adiponectin non-added group) prepared by adding thereto PBS instead of recombinant human adiponectin. After being cultured for 24 hours, the cells were then lysed with a NP40 lysis solution (1% IGEPAL CA630 (Sigma-Aldrich Japan Inc), 150 mM NaCl, 50 mM Tris-HCl (pH 8.0), a protease inhibitor (NACALAI TESQUE, INC.)). Supernatants were collected after performing centrifugation at 100,000×g for 30 min. The supernatants thus collected were used as NP40 soluble fractions when performing immunoprecipitation. Immunoprecipitation was performed using Immunoprecipitation Starter Pack (GE Healthcare Japan Corporation) in accordance with a manual provided by the manufacturer and vender. The anti-α (alpha)-synuclein mouse monoclonal antibody (syn-1, Nippon Becton Dickinson Company, Ltd) was added to the NP40 soluble fractions (200 µg) of both the B103 neuroblastoma cells (α (alpha)S) treated with adiponectin and the B103 neuroblastoma cells (α (alpha)S) non-treated with adiponectin, followed by performing incubation at 4° C. over night. Further, as a control, a mouse IgG1 antibody (DAKO) was added. After completing the aforementioned incubation, 50% suspension of agarose binding body in slurry (Protein G Sepharose 4 Fast Flow) was added so as to further perform incubation at 4° C. for 60 min. Later, immunoprecipitated complexes were collected by centrifugation. The complexes were resuspended in PBS and subjected to centrifugation at 4° C. After performing washing three times, the complexes collected were lysed in 1×SDS sample buffer, and then subjected to western blotting. Here, western blotting was performed in accordance with the procedures described in example 1. When performing western blotting, the anti-phosphorylated tau (Ser 202) antibody (ANASPEC) and the anti-α (alpha)-synuclein mouse monoclonal antibody (syn-1, Nippon Becton Dickinson Company, Ltd) were used as primary antibodies after being appropriately diluted. Further, the HRP labeled anti-rabbit IgG antibody (DAKO) and the HRP labeled anti-mouse IgG antibody (DAKO) were used as secondary antibodies after being appropriately diluted.

1.5 Experiment Regarding Suppression of Expression of Adiponectin Receptor Using siRNA The aforementioned B103 neuroblastoma cells (α (alpha)S) were inoculated on the 6-well plate and cultured to a state of about 30-50% confluence. Later, siRNA of rat adiponectin receptor 1 (Adipo R1) (sc-156024, Santana Cruz Biotechnology, Inc.), siRNA of rat adiponectin receptor 2 (Adipo R2) (sc-156025, Santana Cruz Biotechnology, Inc.) and siRNA of random sequence (mixture of sense siRNA (SEQ. No. 17) and antisense siRNA (SEQ. No. 18)) were transfected using Lipofectamine 2000 (Invitrogen, Life Technologies Japan Ltd.). Six hours later, the medium was replaced with the DMEM containing 10% FBS, and the aforementioned cells were then cultured for 48 hours. Later, the cells were further cultured for 24 hours in a medium prepared by adding recombinant human adiponectin (1_µg/mL, trimer, PROSPEC) to a serum-free medium. As a control, PBS was added to the serum-free DMEM medium instead of recombinant human adiponectin. The aforementioned cells were washed with PBS after being cultured, followed by preparing the TBS soluble fraction, the SDS soluble fraction and the formic acid soluble fraction in accordance with the method described in example 1. Further, western blotting was performed in accordance with the method described in example 1. When performing western blotting, the anti-α (alpha)-synuclein mouse monoclonal antibody (syn-1, Nippon Becton Dickinson Company, Ltd) was used as a primary antibody after being appropriately diluted. Further, the HRP labeled anti-mouse IgG antibody (DAKO) was used as a secondary antibody after being appropriately diluted.

2. Result 2.1 Experiment Regarding Adiponectin Addition (1) (α (Alpha)-Synuclein Aggregation)

Figure 8:
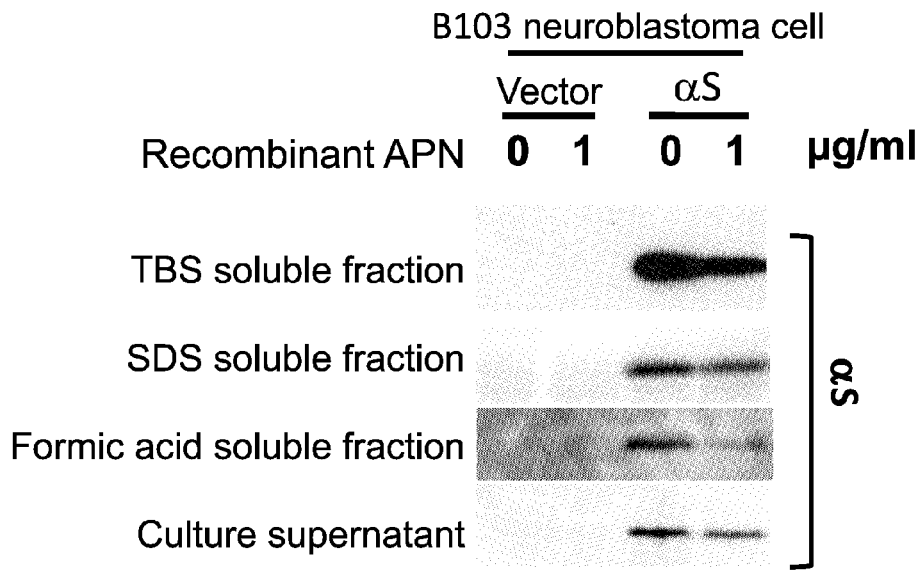
FIG. 8 is a western blot image showing various fractions extracted from the B103 neuroblastoma cells (α (alpha)S) and the B103 neuroblastoma cells (vector), the fractions being detected using anti-α (alpha)-synuclein antibody.

FIG. 8 is a western blot image showing various fractions extracted from the B103 neuroblastoma cells (α (alpha)S) and the B103 neuroblastoma cells (vector), the fractions being detected using anti-α (alpha)-synuclein antibody. As shown in FIG. 8, α (alpha)-synuclein in the formic acid soluble fraction and a culture supernatant had decreased due to the addition of adiponectin. Accordingly, it was indicated that the formation of α (alpha)-synuclein aggregates was suppressed in the presence of adiponectin. Here, cytotoxicity due to the addition of adiponectin was not particularly observed.

2.2 Experiment Regarding Adiponectin Addition (2) (Signal Transduction)

Figure 9A:
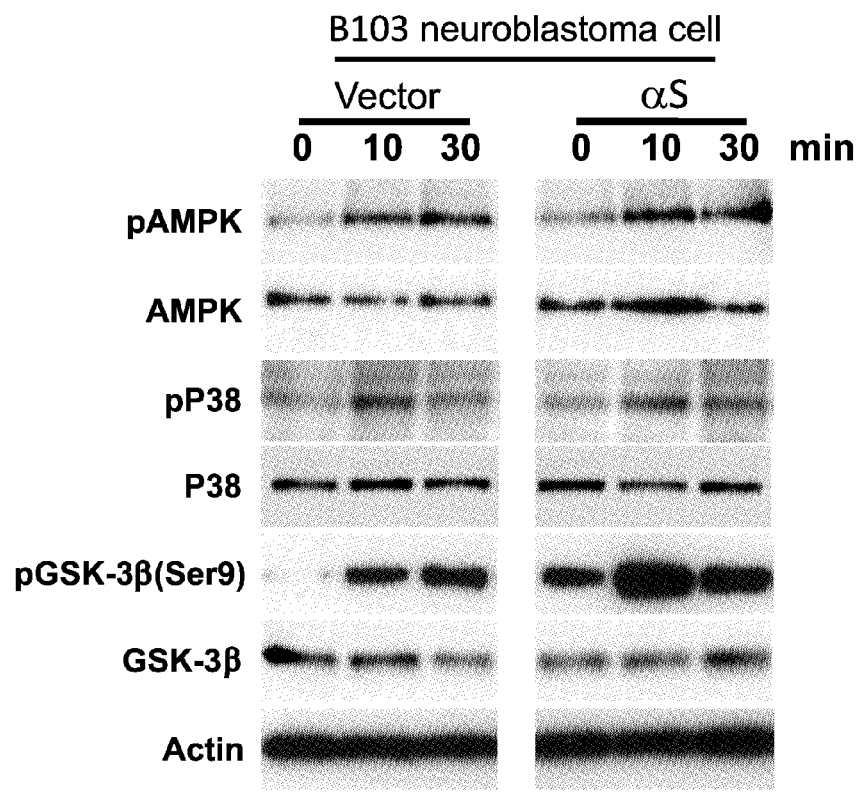
FIG. 9A is a western blot image showing surfactant soluble fractions prepared from the B103 neuroblastoma cells (α (alpha)S) and the B103 neuroblastoma cells (vector), the surfactant soluble fractions being detected using: anti-phospho-AMPKα (alpha) antibody; anti-AMPKα (alpha) antibody; anti-phospho-p38 MAPK antibody; anti-p38α (alpha)/SAPK2a antibody; anti-phospho-GSK-3β (beta) (Ser9) antibody; anti-GSK-3β (beta) antibody; and anti-β (beta)-actin mouse monoclonal antibody.

FIG. 9A is a western blot image showing surfactant soluble fractions prepared from the B103 neuroblastoma cells (α (alpha)S) and the B103 neuroblastoma cells (vector), the surfactant soluble fractions being detected using: the anti-phospho-AMPKα (alpha) antibody; the anti-AMPKα (alpha) antibody; the anti-phospho-p38 MAPK antibody; the anti-p38α (alpha)/SAPK2a antibody; the anti-phospho-GSK-3β (beta) (Ser9) antibody; the anti-GSK-3β (beta) antibody; and the anti-β (beta)-actin mouse monoclonal antibody. As shown in FIG. 9A, phosphorylation of p38 MAPK, AMPK and GSK-3β (beta) had been promoted due to the addition of adiponectin. Accordingly, it was indicated that adiponectin promoted signal transduction effected by p38 MAPK, AMPK and GSK-3β (beta). Here, cytotoxicity due to the addition of adiponectin was not particularly observed.

2.3 Experiment Regarding Addition of p38 MAPK Inhibitor and AMPK Inhibitor

Figure 9B:
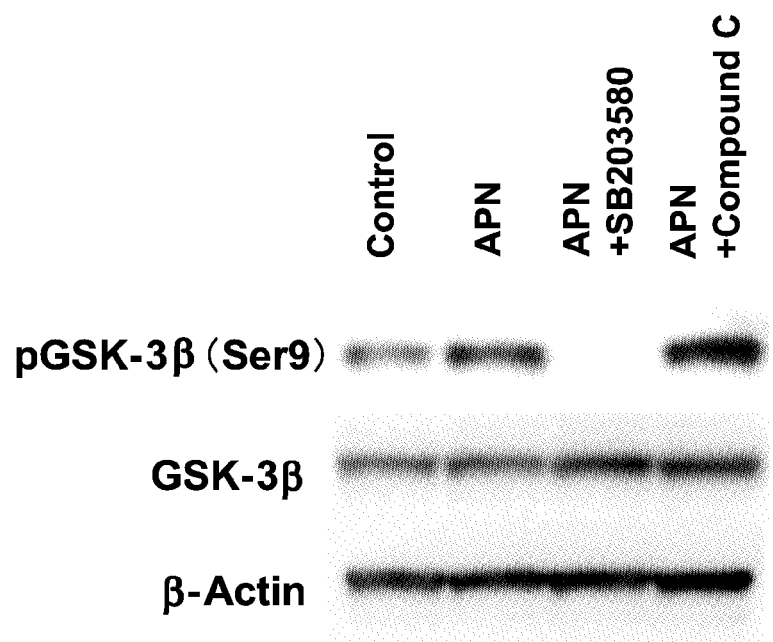
FIG. 9B is a western blot image showing surfactant soluble fractions prepared from the B103 neuroblastoma cells (α (alpha)S) treated with p38 MAPK inhibitor or AMPK inhibitor, the surfactant soluble fractions being detected using anti-phospho-GSK-3β (beta) antibody.

FIG. 9B is a western blot image showing surfactant soluble fractions prepared from the B103 neuroblastoma cells (α (alpha)S) treated with p38 MAPK inhibitor or AMPK inhibitor, the surfactant soluble fractions being detected using the anti-phospho-GSK-3β (beta) antibody. As shown in FIG. 9B, phosphorylated GSK-3β (beta) was detected in the surfactant soluble fractions prepared from the B103 neuroblastoma cells (α (alpha)S) of an adiponectin non-added group (Control), an inhibitor non-added group (APN) and an AMPK inhibitor-treated group (APN+Compound C). However, phosphorylated GSK-3β (beta) was not detected in the surfactant soluble fraction prepared from the B103 neuroblastoma cells (α (alpha)S) of a p38 MAPK inhibitor-treated group (APN+SB203580). Accordingly, it was indicated that promotion of phosphorylation of GSK-3β (beta) by adiponectin depended on p38 MAPK. Further, it was also indicated that the formation of α (alpha)-synuclein aggregates could be suppressed by activating p38 MAPK-mediated signal transduction.

2.4 Experiment Regarding Adiponectin Addition (3) (Tau Phosphorylation)

Figure 10A:
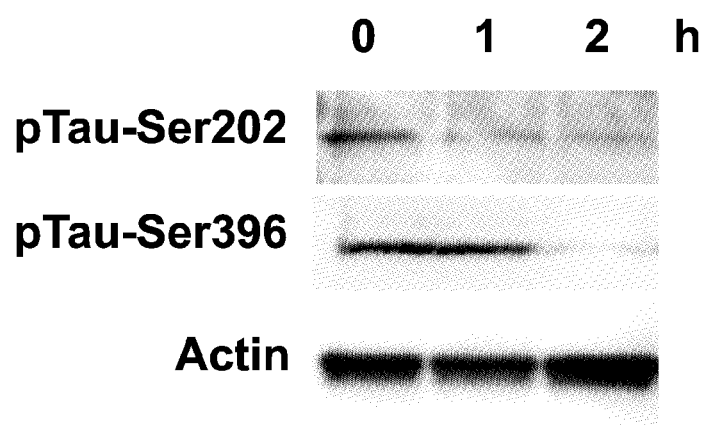
FIG. 10A is a western blot image showing surfactant soluble fractions prepared from the B103 neuroblastoma cells (α (alpha)S), the surfactant soluble fractions being detected using anti-phosphorylated tau (Ser 202) antibody and anti-phosphorylated tau (Ser 396) antibody.

FIG. 10A is a western blot image showing surfactant soluble fractions prepared from the B103 neuroblastoma cells (α (alpha)S), the surfactant soluble fractions being detected using the anti-phosphorylated tau (Ser 202) antibody and the anti-phosphorylated tau (Ser 396) antibody. As shown in FIG. 10A, the amount of phosphorylated tau had decreased due to the addition of adiponectin. Accordingly, it was indicated that adiponectin contributed not only to the suppression of the formation of α (alpha)-synuclein aggregates, but also to the suppression of tau phosphorylation. Further, it was also indicated that p38 MAPK-mediated signal transduction pathways were involved in the suppression of tau phosphorylation, and that tau phosphorylation (tau accumulation) could be suppressed by inhibiting p38 MAPK-mediated signal transduction. Here, cytotoxicity due to the addition of adiponectin was not particularly observed.

2.5 Immunoprecipitation

Figure 10B:
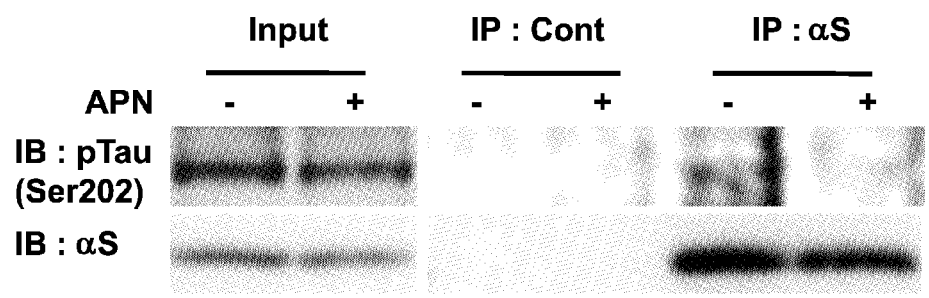
FIG. 10B is a western blot image showing phosphorylated tau (Ser 202) detected by anti-phosphorylated tau (Ser 202) antibody, the phosphorylated tau (Ser 202) being prepared by performing immunoprecipitation, using anti-α (alpha)-synuclein antibody, on an NP40 soluble fraction prepared from the B103 neuroblastoma cells (α (alpha)S).

FIG. 10B is a western blot image showing phosphorylated tau (Ser 202) detected by the anti-phosphorylated tau (Ser 202) antibody, the phosphorylated tau (Ser 202) being prepared by performing immunocoprecipitation, using anti-α (alpha)-synuclein antibody, on the NP40 soluble fraction obtained from the B103 neuroblastoma cells (α (alpha)S). In FIG. 10B, "Input" refers to a non-immunoprecipitated sample, "IP" refers to immunoprecipitation, and "IB" refers to immunoblot. As shown in FIG. 10B, as for the adiponectin-non-added group in which immunoprecipitation was performed using anti-α (alpha)-synuclein antibody, phosphorylated tau coprecipitated with α (alpha)-synuclein. Further, with regard to the adiponectin-added group in which immunoprecipitation was performed using anti-α (alpha)-synuclein antibody, phosphorylated tau did not coprecipitate with α (alpha)-synuclein. Accordingly, it was indicated that adiponectin was also effective in suppressing the formation of tau aggregates.

Figure 11:
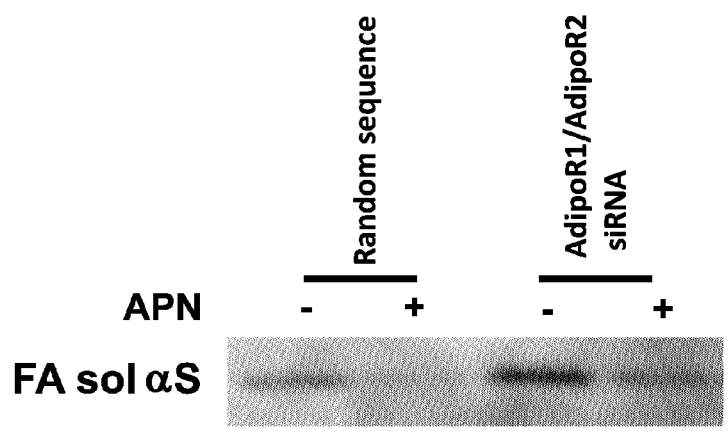
FIG. 11 is a western blot image showing a formic acid soluble fraction prepared from the B103 neuroblastoma cells (α (alpha)S) transfected with siRNA, the formic acid soluble fraction being detected using anti-phosphorylated α (alpha)-synuclein antibody.

2.6 Experiment Regarding Suppression of Expression of Adiponectin Receptor Using siRNA FIG. 11 is a western blot image showing a formic acid soluble fraction prepared from the B103 neuroblastoma cells (α (alpha)S) transfected with siRNA, the formic acid soluble fraction being detected using anti-phosphorylated α (alpha)-synuclein antibody. As shown in FIG. 11, the amount of phosphorylated α (alpha)-synuclein increased in the experimental groups in which siRNA of adiponectin receptors 1 and 2 had been transfected, as compared to the experimental groups in which siRNA of random sequence had been transfected. Accordingly, it was indicated that the formation of α (alpha)-synuclein aggregates was suppressed by adiponectin through downstream signal transduction pathways of adiponectin receptor.

Experimental Example 9

Experiment Regarding Single Administration of Globular Adiponectin to α (Alpha)S Tg Mouse (Evaluation of gAPN Distribution after Nasal Administration)

1. Material and Method 1.1 Single Administration of Globular Adiponectin

An α (alpha)S tg mouse was distinguished in accordance with the method described in example 2. Either globular adiponectin with FLAG-tagged N-terminal (FLAG-gAPN) or PBS was nasally administered to the α (alpha)S tg mouse on days 0, 3, 6, 9, 12, 15, 18 and 21. When performing nasal administration, 10 μL of a transmucosal absorption enhancer (PBS containing 5 mg/mL poly-L-arginine hydrochloride (molecular mass>70,000 (Sigma-Aldrich Japan Inc.)) was nasally administered to the mouse. Half an hour later, either 10 μL of the aforementioned globular adiponectin (PBS containing 1 mg/ml FLAG-gAPN (AdipoGen)) or 10 μL of PBS was nasally administered to the mouse. Half an hour later, the mouse was euthanized in accordance with the method described in example 2, followed by collecting a brain sample thereof.

1.2 Fluorescence Immunohistochemical Staining

Fluorescence immunohistochemical staining was performed in a standard manner known to those skilled in the art. Briefly, a hemisphere of the brain sample was treated with a 20% sucrose/0.01 M PBS solution, followed by being embedded in Tissue-Tek OCT compound 4583 (SAKURA SEIKI Co., Ltd.) and then frozen by liquid nitrogen. Thin sliced sections of the brain sample were prepared at a thickness of 7 μm and then placed on a glass slide. After being air-dried, the thin sliced sections were hydrated with 0.01 M PBS, and then subjected to blocking for 30 min using 10% goat normal serum (Vector Laboratories, Inc.)/TBS (25 mM Tris-HCl (pH 7.5), 0.15 M NaCl). Later, the thin sliced sections were incubated at 4° C. overnight with a primary antibody (anti-DDDDK-tag antibody, MEDICAL&BIOLOGICAL LABORATORIES CO., LTD.) diluted with 0.1% bovine serum albumin (BSA)/TBS. After washing, the thin sliced sections were then incubated for an hour at room temperature with a secondary antibody (Alexa Fluor 488 labeled antibody, Invitrogen, Life Technologies Japan Ltd.) diluted with 0.1% BSA/TBS. After embedding, the confocal laser scanning microscope (FV1000, Olympus Corporation) was used to observe the thin sliced sections.

2. Result

Fluorescence Immunohistochemical Staining

Figure 12:
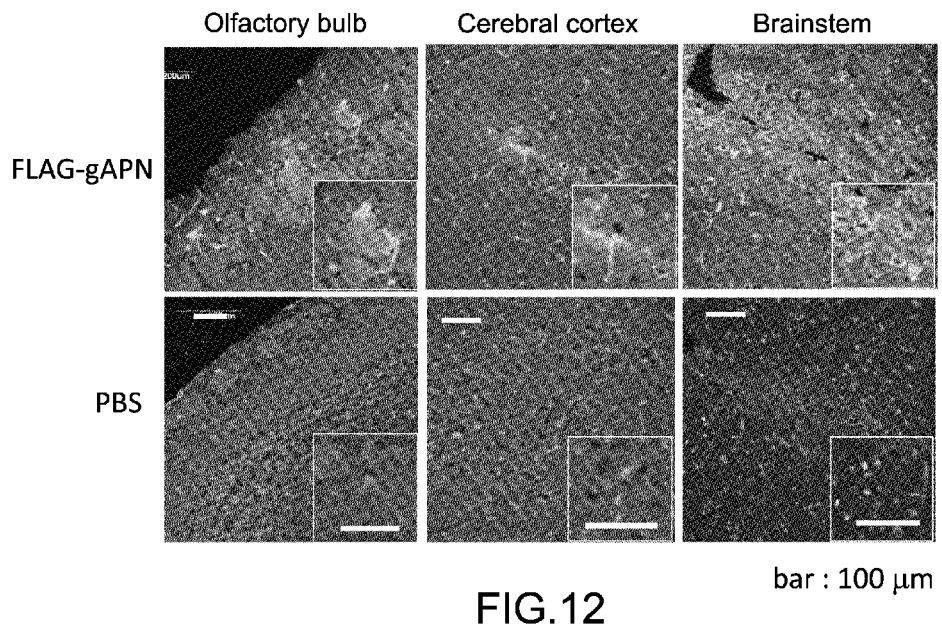
FIG. 12 is a set of confocal microscopic photographs of brain samples (olfactory bulb, cerebral cortex and brainstem) of an α (alpha)S tg mouse and a non tg mouse that were stained by fluorescence immunohistochemical staining.

FIG. 12 is a set of confocal microscopic photographs of the brain samples (olfactory bulb, cerebral cortex and brainstem) of an α (alpha)S tg mouse and a non tg mouse that were stained by fluorescence immunohistochemical staining. As shown in FIG. 12, FLAG-gAPN was detected in olfactory bulb, cerebral cortex and brainstem. Further, FLAG-gAPN was also detected in other brain tissues (not shown). Accordingly, it became evident that FLAG-gAPN had been distributed in the brain of the mouse after nasal administration. Here, side effects caused by the single administration of globular adiponectin were not observed particularly.

Experimental Example 10

Experiment Regarding Continuous Administration of Globular Adiponectin to α (Alpha)S tg Mouse 1. Material and Method 1.1 Continuous Administration of Globular Adiponectin An α (alpha)S tg mouse and a non tg mouse were distinguished in accordance with the method described in example 2. Globular adiponectin (gAPN) was nasally administered to the α (alpha)S tg mouse and the non tg mouse on days 0, 3, 6, 9, 12, 15, 18 and 21. Further, as a control, PBS was nasally administered to the α (alpha)S tg mouse and the non tg mouse on days 0, 3, 6, 9, 12, 15, 18 and 21. When performing nasal administration, 10 µL of the transmucosal absorption enhancer (PBS containing 5 mg/mL poly-L-arginine hydrochloride (molecular mass>70,000 (Sigma-Aldrich Japan Inc.)) was nasally administered to the mouse. Half an hour later, either 10 µL of globular adiponectin (PBS containing 1 mg/mL gAPN (Prospec)) or 10 µL of PBS was nasally administered to the mouse. On day 22 of nasal administration, the aforementioned mouse was euthanized in accordance with the method described in example 2, followed by collecting brain samples thereof. The hemispheres used for pathological analysis were immersion-fixed using 4% paraformaldehyde, followed by being embedded in paraffin. The other hemispheres used for western blotting were frozen by liquid nitrogen and stored at −80° C.

1.2 Immunohistochemical Staining

Immunohistochemical staining was performed in a standard manner known to those skilled in the art. Briefly, thin sliced sections were prepared at a thickness of 4 µm, using the brain samples embedded in paraffin. After being deparaffinized, the thin sliced sections were placed in a 10 mM sodium citrate buffer solution (pH 6.0) to be subjected to an antigen activation treatment (95° C., 10 min) using microwave (MW). After completing the antigen activation treatment, the thin sliced sections were further treated for 15 min with methanol containing 3% hydrogen peroxide. After washing, the thin sliced sections were then subjected to blocking for 30 min, using 10% goat normal serum (Vector Laboratories, Inc.)/TBS (25 mM Tris-HCl (pH 7.5), 0.15 M NaCl). Later, the thin sliced sections were incubated overnight at 4° C. with a primary antibody (anti-α (alpha)-synuclein antibody or anti-GFAP antibody) diluted with 0.1% bovine serum albumin (BSA)/TBS. After washing, the thin sliced sections were further incubated for 20 min at room temperature with a secondary antibody (biotin labeled anti-mouse IgG antibody (Vector Laboratories, Inc.)) diluted with 0.1% BSA/TBS. When performing staining, there were used ABC kit (Vector Laboratories, Inc.) and 3,3'-diaminobenzidine tetrahydrochloride (DAB). After completing staining, the thin sliced sections were observed using a microscope.

1.3 Detection of GFAP in Surfactant Insoluble Fraction

The brain sample was homogenized in the cell lysis solution (1% TritonX-100, 1% Nonidet P-40, 50 mM HEPES, 150 mM NaCl, 10% glycerol, 1.5 mM $MgCl_2$, 1 mM EGTA, 100 mM sodium fluoride, a protease inhibitor (NACALAI TESQUE, INC.)), followed by being centrifuged at 100,000× g, 4° C. for 30 min. Precipitates were used as surfactant insoluble fractions when performing western blotting. Here, western blotting was performed in accordance with the method described in example 1. Particularly, when performing western blotting, the anti-GFAP antibody (Progen) and the anti-β (beta)-actin mouse monoclonal antibody (C-15, Sigma-Aldrich Japan Inc.) were used as primary antibodies after being appropriately diluted. Further, the HRP labeled anti-mouse IgG antibody (DAKO) was used as a secondary antibody after being appropriately diluted.

1.4 Evaluation of α (Alpha)-Synuclein Aggregation in Various Fractions

The TBS soluble fraction, the SDS soluble fraction and the formic acid soluble fraction were prepared from the cerebral cortex of the brain sample in accordance with the method described in example 1. Here, western blotting was performed in accordance with the method described in example 1. When performing western blotting, the anti-α (alpha)-synuclein mouse monoclonal antibody (syn-1, Nippon Becton Dickinson Company, Ltd) was used as a primary antibody after being appropriately diluted. Further, the HRP labeled anti-mouse IgG antibody (DAKO) was used as a secondary antibody after being appropriately diluted.

2 Result 2.1 Immunohistochemical Staining

Figure 13A:
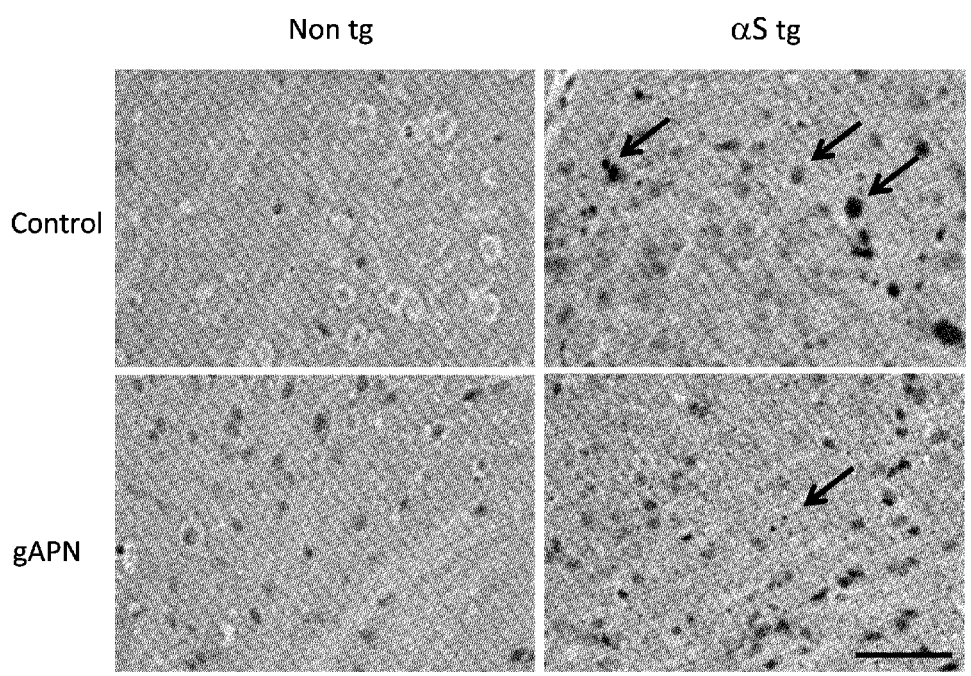
FIG. 13A is a set of microscopic photographs of brain samples (thalamus) of the α (alpha)S tg mouse and the non tg mouse that were stained by immunohistochemical staining.
Figure 13B:
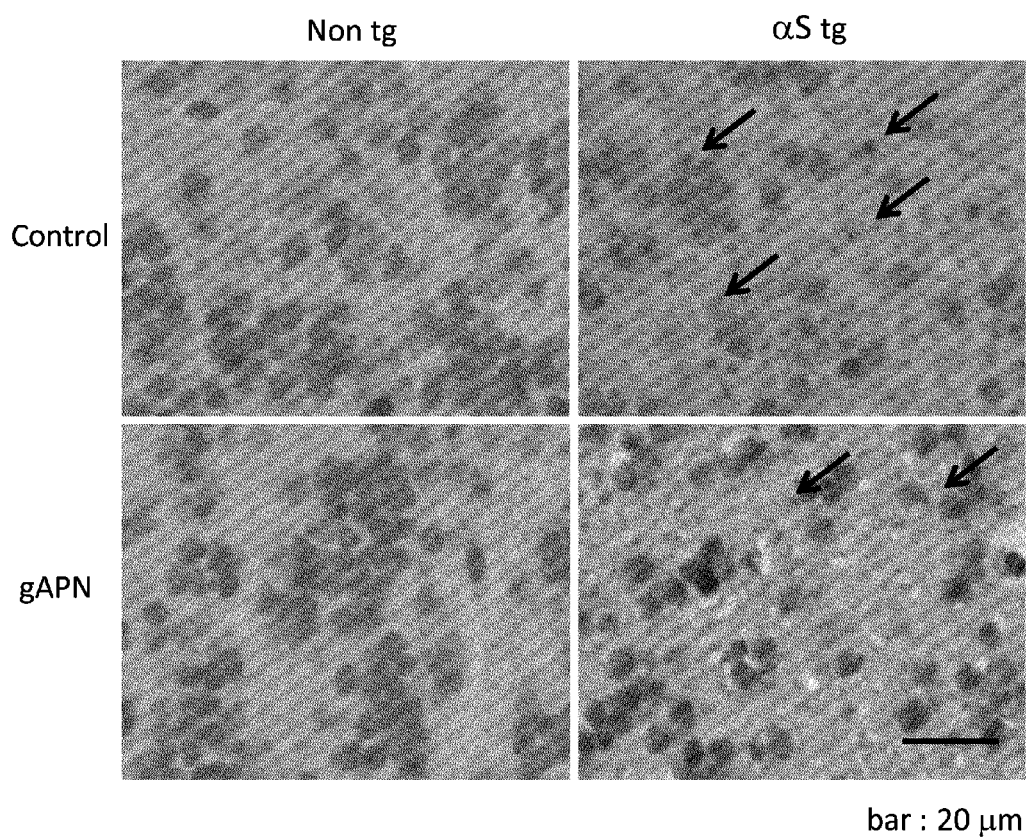
FIG. 13B is a set of microscopic photographs of brain samples (olfactory bulb) of the α (alpha)S tg mouse and the non tg mouse that were stained by immunohistochemical staining.
Figure 13C:
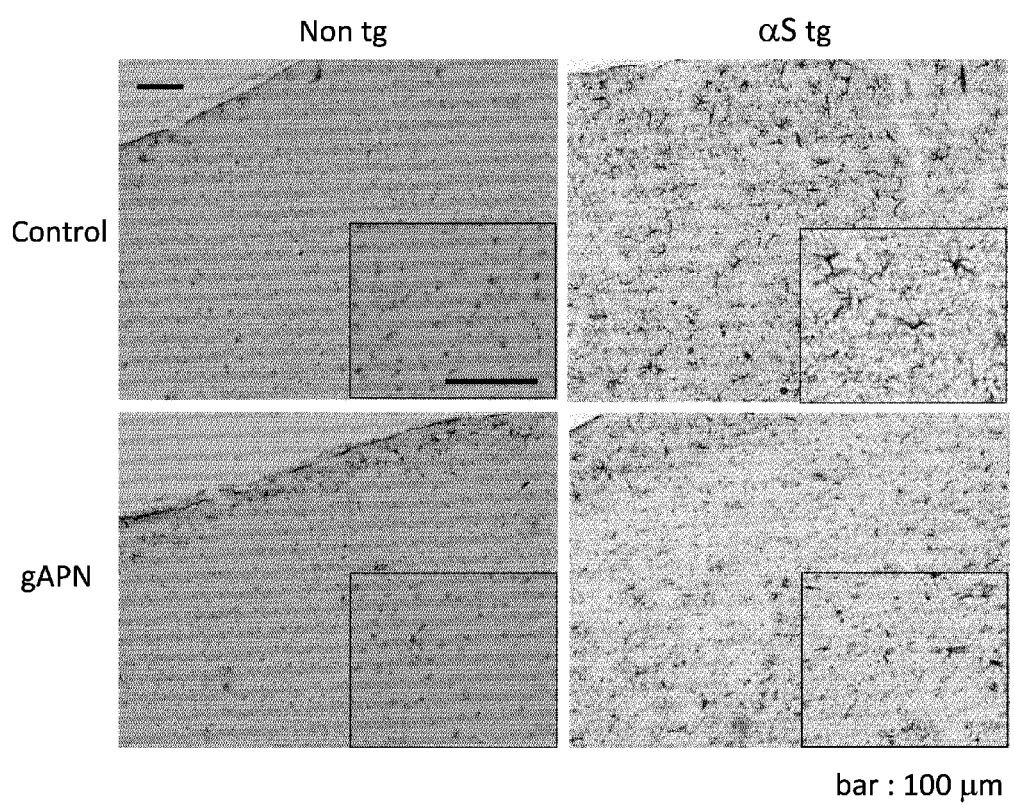
FIG. 13C is a set of microscopic photographs of brain samples (cerebral cortex) of the α (alpha)S tg mouse and the non tg mouse that were stained by immunohistochemical staining.

FIG. 13A is a set of microscopic photographs of the brain samples (thalamus) of the α (alpha)S tg mouse and the non tg mouse that were stained by immunohistochemical staining. As shown in FIG. 13A, α (alpha)-synuclein aggregates were detected in the α (alpha)S tg mouse belonging to a gAPN non-administration group. However, α (alpha)-synuclein aggregates were hardly detected in the α (alpha)S tg mouse belonging to a gAPN-administered group. FIG. 13B is a set of microscopic photographs of the brain samples (olfactory bulb) of the α (alpha)S tg mouse and the non tg mouse that were stained through immunohistochemical staining. As shown in FIG. 13B, α (alpha)-synuclein aggregates were detected in the α (alpha)S tg mouse belonging to the gAPN non-administration group. However, α (alpha)-synuclein aggregates were hardly detected in the α (alpha)S tg mouse belonging to the gAPN-administered group. FIG. 13C is a set of microscopic photographs of the brain samples (cerebral cortex) of the α (alpha)S tg mouse and the non tg mouse that were stained by immunohistochemical staining. As shown in FIG. 13C, growth of astrocyte was detected in the α (alpha)S tg mouse belonging to the gAPN non-administration group. However, the growth of astrocyte was hardly detected in the α (alpha)S tg mouse belonging to the gAPN-administered group. Accordingly, it was indicated that gAPN was capable of suppressing the formation of α (alpha)-synuclein aggregates and the growth of astrocyte in the brain. Based on these results, it became evident that gAPN, as is the case with adiponectin, was also capable of suppressing the formation of α (alpha)-synuclein aggregates. Further, it was also indicated that gAPN could be used to treat, prevent and/or alleviate neurodegenerative diseases involving aggregate formation, since gAPN suppressed the formation of α (alpha)-synuclein aggregates and/or a decrease in proteasome activity. Here, adverse effects caused by the continuous administration of globular adiponectin were not observed particularly.

2.2 Detection of GFAP in Surfactant Insoluble Fraction

Figure 14A:
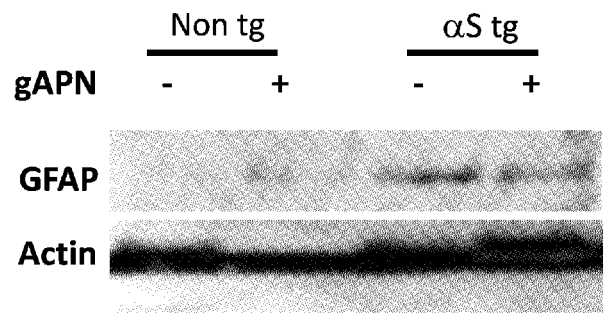
FIG. 14A is a western blot image showing surfactant insoluble fractions prepared from the α (alpha)S tg mouse and the non tg mouse, the surfactant insoluble fractions being detected using anti-GFAP antibody.

FIG. 14A is a western blot image showing surfactant insoluble fractions prepared from the α (alpha)S tg mouse and the non tg mouse, the surfactant insoluble fractions being detected using the anti-GFAP antibody. As shown in FIG. 14A, GFAP was detected in the α (alpha)S tg mouse belonging to the gAPN-administered group and the α (alpha)S tg mouse belonging to the gAPN non-administration group. However, GFAP was observed less in the α (alpha)S tg mouse belonging to the gAPN-administered group than in the α (alpha)S tg mouse belonging to the gAPN non-administration group. Accordingly, it became evident that abnormal activation of astrocyte was suppressed in the α (alpha)S tg mouse belonging to the gAPN-administered group. It was indicated that gAPN suppressed the activation of astrocyte that was induced by the neurotoxicity of the accumulated α (alpha)-synuclein.

2.3 Evaluation of α (Alpha)-Synuclein Aggregation in Various Fractions

Figure 14B:
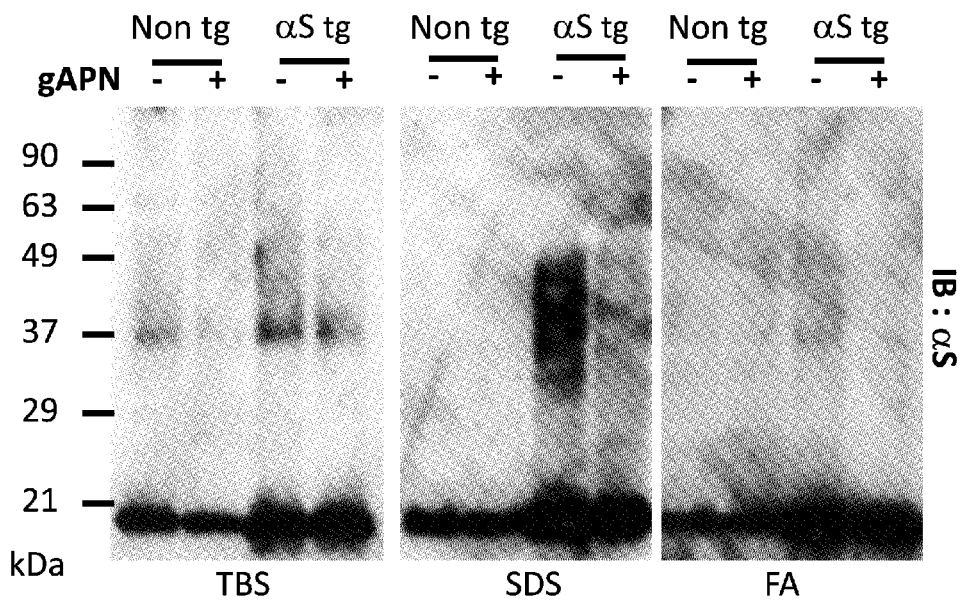
FIG. 14B is a western blot image showing various extracted fractions prepared from the α (alpha)S tg mouse and the non tg mouse, the extracted fractions being detected using anti-α (alpha)-synuclein antibody.

FIG. 14B is a western blot image showing various extracted fractions prepared from the α (alpha)S tg mouse and the non tg mouse, the extracted fractions being detected using anti-α (alpha)-synuclein antibody. As shown in FIG. 8, the amount of α (alpha)-synuclein aggregates decreased significantly in the SDS soluble fraction prepared from the α (alpha)S tg mouse belonging to the gAPN-administered group. Accordingly, it was indicated that the formation of α (alpha)-synuclein aggregates was suppressed in the presence of adiponectin.

The invention claimed is:

1. A method for treating α(alpha)-synucleinopathy, which comprises administering an effective dose of globular adiponectin, to the central nervous system of a subject in need thereof.

2. The method according to claim 1, wherein the α(alpha)-synucleinopathy is selected from the group consisting of Parkinson disease, dementia with Lewy bodies, Alzheimer disease and multiple system atrophy.

3. The method according to claim 1, wherein the α(alpha)-synucleinopathy is selected from the group consisting of Parkinson disease, dementia with Lewy bodies and multiple system atrophy.

4. The method according to claim 1, wherein said step of administering is by nasal administration.

5. The method according to claim 1, wherein the amino acid sequence of globular adiponectin is SEQ ID NO. 24.

6. The method according to claim 1, wherein the globular adiponectin is administered to the cerebral ventricles of the subject in need thereof.

7. The method according to claim 1, wherein the α(alpha)-synucleinopathy is Parkinson disease.

8. The method according to claim 1, wherein the α(alpha)-synucleinopathy is dementia with Lewy bodies.

9. The method according to claim 1, wherein the α(alpha)-synucleinopathy is Alzheimer disease.

10. The method according to claim 1, wherein the α(alpha)-synucleinopathy is multiple system atrophy.

11. A method for suppressing a progression of α(alpha)-synucleinopathy, which comprises administering an effective dose of globular adiponectin to the central nervous system of a subject in need thereof.

12. The method according to claim 11, wherein the α(alpha)-synucleinopathy is selected from the group consisting of Parkinson disease, dementia with Lewy bodies, Alzheimer disease and multiple system atrophy.

13. The method according to claim 11, wherein the α(alpha)-synucleinopathy is selected from the group consisting of Parkinson disease, dementia with Lewy bodies and multiple system atrophy.

14. The method according to claim 11, wherein said step of administering is by nasal administration.

15. The method according to claim 11, wherein the amino acid sequence of globular adiponectin is SEQ ID NO. 24.

16. The method according to claim 11, wherein the globular adiponectin is administered to the cerebral ventricles of the subject in need thereof.

17. The method according to claim 11, wherein the α(alpha)-synucleinopathy is Parkinson disease.

18. The method according to claim 11, wherein the α(alpha)-synucleinopathy is dementia with Lewy bodies.

19. The method according to claim 11, wherein the α(alpha)-synucleinopathy is Alzheimer disease.

20. The method according to claim 11, wherein the α(alpha)-synucleinopathy is multiple system atrophy.

* * * * *